US010548737B2

(12) United States Patent
Hodorek et al.

(10) Patent No.: US 10,548,737 B2
(45) Date of Patent: *Feb. 4, 2020

(54) REVERSE SHOULDER PROSTHESES WITH ANTI-ROTATION FEATURES

(71) Applicant: Tornier Orthopedics Ireland Ltd., Cork (IE)

(72) Inventors: Brian C. Hodorek, Warsaw, IN (US); Shawn Martin Gargac, Fort Wayne, IN (US)

(73) Assignee: Tornier Orthopedics Ireland Ltd., Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/336,593

(22) Filed: Oct. 27, 2016

(65) Prior Publication Data

US 2017/0049573 A1 Feb. 23, 2017

Related U.S. Application Data

(63) Continuation of application No. 14/265,284, filed on Apr. 29, 2014, now Pat. No. 9,498,344, which is a
(Continued)

(30) Foreign Application Priority Data

Dec. 21, 2011 (EP) .................................... 11306724
Dec. 21, 2011 (EP) .................................... 11306725
(Continued)

(51) Int. Cl.
*A61F 2/40* (2006.01)
*A61F 2/46* (2006.01)
(Continued)

(52) U.S. Cl.
CPC .......... *A61F 2/4059* (2013.01); *A61B 17/164* (2013.01); *A61B 17/1684* (2013.01);
(Continued)

(58) Field of Classification Search
CPC ............................................... A61F 2/40–4081
See application file for complete search history.

(56) References Cited

U.S. PATENT DOCUMENTS

| 4,310,931 A | 1/1982 | Muller |
| 5,910,171 A | 6/1999 | Kummer et al. |

(Continued)

FOREIGN PATENT DOCUMENTS

| DE | 102 50 390 | 5/2004 |
| DE | 10 2005 003 097 | 7/2006 |

(Continued)

OTHER PUBLICATIONS

International Search Report and Written Opinion for PCT/EP2012/0171618 dated Apr. 12, 2013 in 20 pages.
(Continued)

*Primary Examiner* — Marcia L Watkins
(74) *Attorney, Agent, or Firm* — Knobbe Martens Olson & Bear, LLP

(57) ABSTRACT

A modular reverse shoulder prosthesis according to embodiments of the present invention includes a stem having a proximal taper and a primary stem axis, the proximal taper extending from the stem about a metaphyseal axis, the metaphyseal axis at an angle with respect to the primary stem axis, a metaphysis having a proximal end, a distal end, a first aperture in the distal end configured to be placed over the proximal taper, and a second aperture in the proximal end having an insert axis that is eccentrically offset from the metaphyseal axis, the metaphysis configured for attachment to the stem at any rotational position of the metaphysis about
(Continued)

the metaphyseal axis, and a reverse insert, the reverse insert having a proximal end and a distal end, wherein the proximal end comprises a concave cup formed about a cup axis and configured to receive a glenosphere, and wherein the distal end comprises a locking protrusion, wherein the locking protrusion has an outer surface with a cross-sectional shape that is rotationally symmetrical about the insert axis with respect to a corresponding inner surface of the second aperture, wherein the rotational symmetry has an order of six, seven, eight, nine, or ten.

22 Claims, 28 Drawing Sheets

Related U.S. Application Data continuation of application No. PCT/EP2012/071618, filed on Oct. 31, 2012.

(60) Provisional application No. 61/596,148, filed on Feb. 7, 2012, provisional application No. 61/553,720, filed on Oct. 31, 2011.

(30) Foreign Application Priority Data

Dec. 21, 2011 (EP) ..................................... 11306727
Dec. 21, 2011 (EP) ..................................... 11306728

(51) Int. Cl.
*A61B 17/88* (2006.01)
*A61B 17/17* (2006.01)
*A61B 17/16* (2006.01)
*A61B 90/00* (2016.01)
*A61F 2/30* (2006.01)

(52) U.S. Cl.
CPC .......... *A61B 17/17* (2013.01); *A61B 17/1778* (2016.11); *A61B 17/8875* (2013.01); *A61F 2/40* (2013.01); *A61F 2/4014* (2013.01); *A61F 2/4612* (2013.01); *A61F 2/4637* (2013.01); *A61B 2017/1602* (2013.01); *A61B 2090/034* (2016.02); *A61F 2/4657* (2013.01); *A61F 2002/3054* (2013.01); *A61F 2002/30332* (2013.01); *A61F 2002/30377* (2013.01); *A61F 2002/30507* (2013.01); *A61F 2002/30604* (2013.01); *A61F 2002/30607* (2013.01); *A61F 2002/4022* (2013.01); *A61F 2002/4062* (2013.01); *A61F 2002/4619* (2013.01); *A61F 2002/4641* (2013.01)

(56) References Cited

U.S. PATENT DOCUMENTS

| | | | |
|---|---|---|---|
| 6,165,224 A | 12/2000 | Tornier | |
| 6,187,012 B1 | 2/2001 | Masini | |
| 6,197,062 B1 | 3/2001 | Fenlin | |
| 6,228,119 B1 | 5/2001 | Ondrla et al. | |
| 6,334,874 B1 | 1/2002 | Tornier et al. | |
| 6,436,147 B1 | 8/2002 | Zweymuller | |
| 6,648,894 B2 | 11/2003 | Abdelgany et al. | |
| 6,673,114 B2 | 1/2004 | Hartdegen et al. | |
| 6,899,736 B1 | 5/2005 | Rauscher et al. | |
| 6,942,699 B2 | 9/2005 | Stone et al. | |
| 7,001,389 B1 | 2/2006 | Navarro et al. | |
| 7,011,686 B2 | 3/2006 | Ball et al. | |
| 7,166,132 B2 | 1/2007 | Callaway et al. | |
| 7,175,663 B1 | 2/2007 | Stone | |
| 7,309,360 B2 | 12/2007 | Tornier et al. | |
| 7,445,638 B2 | 11/2008 | Benguin et al. | |
| 7,621,961 B2 | 11/2009 | Stone et al. | |
| 7,802,503 B2 | 9/2010 | Couvillion et al. | |
| 7,819,923 B2 | 10/2010 | Stone et al. | |
| 8,062,376 B2 | 11/2011 | Shultz et al. | |
| 8,070,820 B2 | 12/2011 | Winslow et al. | |
| 8,231,684 B2 | 7/2012 | Mutchler et al. | |
| 8,236,059 B2 | 8/2012 | Stone et al. | |
| 8,357,204 B2 | 1/2013 | Ragbir | |
| 8,512,410 B2 | 8/2013 | Metcalfe et al. | |
| 8,663,333 B2 | 3/2014 | Metcalfe et al. | |
| 8,795,379 B2 | 8/2014 | Smith et al. | |
| 8,906,103 B2 | 12/2014 | Stone et al. | |
| 9,241,803 B2 | 1/2016 | Stone et al. | |
| 9,283,083 B2 | 3/2016 | Winslow et al. | |
| 9,326,862 B2 | 5/2016 | Smith et al. | |
| 9,498,344 B2 | 11/2016 | Hodorek et al. | |
| 9,566,162 B2 | 2/2017 | Isch | |
| 9,844,439 B2 | 12/2017 | Katrana et al. | |
| 10,034,759 B2 | 7/2018 | Deransart et al. | |
| 2001/0010023 A1 | 7/2001 | Schwartz et al. | |
| 2001/0011193 A1 | 8/2001 | Nogarin | |
| 2002/0156534 A1 | 10/2002 | Grusin et al. | |
| 2003/0028253 A1 | 2/2003 | Stone et al. | |
| 2003/0097183 A1 | 5/2003 | Rauscher et al. | |
| 2004/0064190 A1 | 4/2004 | Ball et al. | |
| 2005/0071014 A1 | 3/2005 | Barnett et al. | |
| 2006/0020344 A1 | 1/2006 | Shultz et al. | |
| 2006/0069445 A1* | 3/2006 | Ondrla ...................... | A61F 2/40 623/19.12 |
| 2007/0162140 A1 | 7/2007 | McDevitt | |
| 2007/0173945 A1 | 7/2007 | Wiley et al. | |
| 2007/0179624 A1 | 8/2007 | Stone et al. | |
| 2007/0225821 A1 | 9/2007 | Reubelt et al. | |
| 2008/0183297 A1 | 7/2008 | Boileau et al. | |
| 2009/0265010 A1 | 10/2009 | Angibaud et al. | |
| 2009/0281630 A1 | 11/2009 | Delince et al. | |
| 2010/0049327 A1 | 2/2010 | Isch et al. | |
| 2010/0114326 A1 | 5/2010 | Winslow et al. | |
| 2011/0029089 A1 | 2/2011 | Giuliani et al. | |
| 2011/0060417 A1 | 3/2011 | Simmen et al. | |
| 2011/0125285 A1 | 5/2011 | Ragbir | |
| 2012/0143204 A1 | 6/2012 | Blaycock et al. | |
| 2012/0253350 A1 | 10/2012 | Anthony et al. | |
| 2012/0253467 A1 | 10/2012 | Frankle | |
| 2013/0090736 A1 | 4/2013 | Katrana et al. | |
| 2013/0197652 A1 | 8/2013 | Ekelund et al. | |
| 2013/0289738 A1 | 10/2013 | Humphrey | |
| 2013/0325134 A1 | 12/2013 | Viscardi et al. | |
| 2014/0236304 A1 | 8/2014 | Hodorek et al. | |
| 2015/0265411 A1 | 9/2015 | Deransart et al. | |
| 2016/0213480 A1 | 7/2016 | Stone et al. | |
| 2016/0262902 A1 | 9/2016 | Winslow et al. | |
| 2016/0361173 A1 | 12/2016 | Reubelt et al. | |
| 2017/0030449 A1 | 11/2017 | Deransart et al. | |
| 2018/0280152 A1 | 10/2018 | Mutchler et al. | |
| 2018/0325687 A1 | 11/2018 | Deransart et al. | |

FOREIGN PATENT DOCUMENTS

| | | |
|---|---|---|
| DE | 102008010478 A1 | 8/2009 |
| EP | 0898946 A1 | 3/1999 |
| EP | 1093777 | 4/2001 |
| EP | 1 402 854 | 3/2004 |
| EP | 1472999 A1 | 3/2004 |
| EP | 1415621 A2 | 5/2004 |
| EP | 1 520 562 | 4/2005 |
| EP | 1520560 B1 | 10/2006 |
| EP | 1 782 765 | 5/2007 |
| EP | 1048274 | 9/2012 |
| EP | 2 604 227 | 6/2013 |
| EP | 2604225 A1 | 6/2013 |
| FR | 2652498 A1 | 4/1991 |
| FR | 2 758 256 | 7/1998 |
| FR | 2773469 A1 | 7/1999 |
| FR | 2 932 678 | 12/2011 |
| WO | WO 93/09733 A1 | 5/1993 |
| WO | WO 96/17553 | 6/1996 |
| WO | WO 2003/005933 | 1/2003 |
| WO | WO 2004/080331 | 9/2004 |

(56) References Cited

FOREIGN PATENT DOCUMENTS

| WO | WO 2007/084939 | 7/2007 |
|----|----------------|--------|
| WO | WO 2007/082925 | 10/2007 |
| WO | WO 2008/000928 A2 | 1/2008 |
| WO | WO 2008/050091 | 5/2008 |
| WO | WO 2008/109751 | 9/2008 |
| WO | WO 2013/064569 | 5/2013 |
| WO | WO 2014/067961 | 5/2014 |
| WO | WO 2014/178706 | 11/2014 |
| WO | WO 2015/112307 | 7/2015 |
| WO | WO 2016/094739 | 6/2016 |
| WO | WO 2017/184792 | 10/2017 |

OTHER PUBLICATIONS

European Search Report for EP Application No. 11306724.3 dated May 25, 2012 in 6 pages.
Biomet Orthopedics, "Comprehensive® Shoulder System, Surgical Technique", 2007.
Delta, Delta CTA Reverse Shoulder Prosthesis, Surgical Technique, DePuy a Johnson & Johnson company, 2004.
Depuy, "GlobalTM Fx Shoulder Fracture System, Surgical Technique", 1999.
Depuy Synthes, "Global® UNITE Platform Shoulder System, Product Rationale & Surgical Technique", 2013.
DJO Surgical, "DJO Surgical Shoulder Solutions—Reaching Higher by Design", 2013.
Exactech, "Equinoxe Platform Shoulder System", 2014.
FH Orthopedics, "ARROW, Prothese d'epaule Universelle (Universal shoulder prosthesis)", Nov. 2009.
Integra, TitanTM Reverse Shoulder System, Surgical Technique, 2013.
Levy et al., "Reverse Shoulder Prosthesis for Acute Four-Part Fracture: Tuberosity Fixation Using a Horseshoe Graft", J Orthop Trauma, vol. 25, No. 5, May 2011.
Stryker Orthopaedics, "ReUnion Fracture System Surgical Protocol", 2007.
Tornier, "Aequalis Ascend Flex Convertible Shoulder System", Feb. 8, 2016.
Zimmer, "Anatomical ShoulderTM Fracture System, Surgical Technique", 2010.
Zimmer®, "Trabecular MetalTM Humeral Stem—Enabling fracture healing", 2009.

* cited by examiner

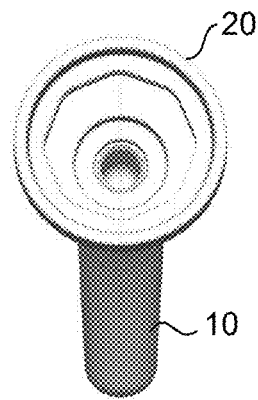 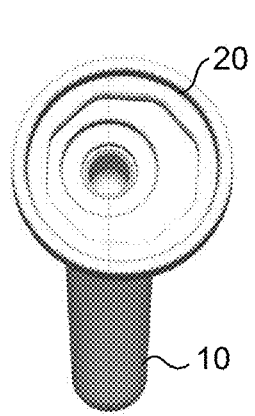 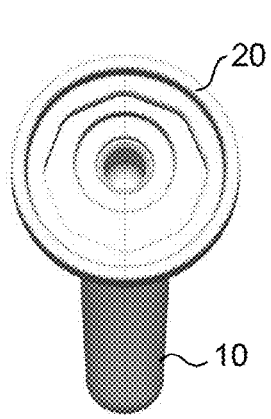 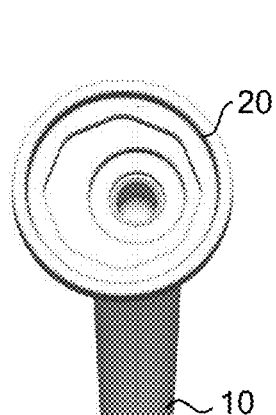
FIG. 32  FIG. 33  FIG. 34  FIG. 35
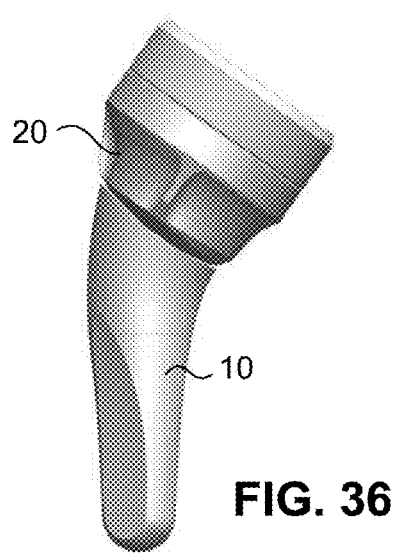 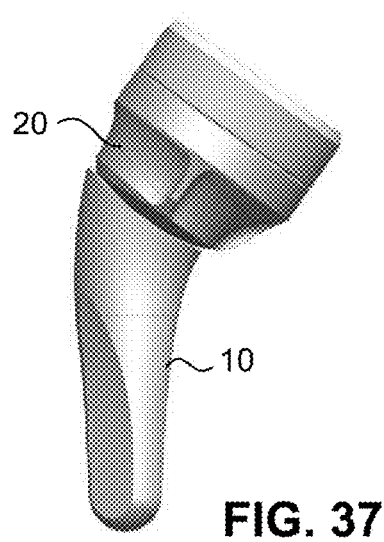
FIG. 36  FIG. 37

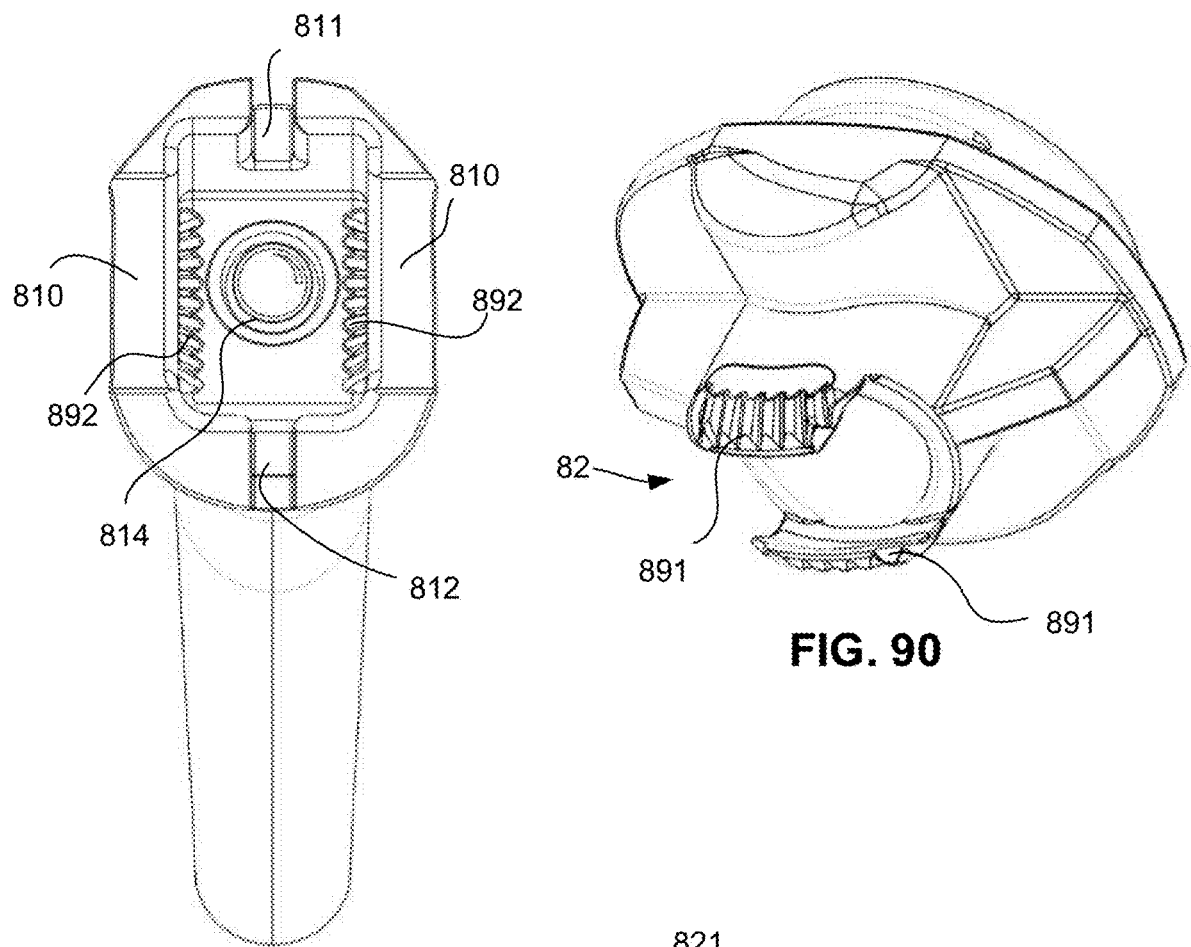
FIG. 89
FIG. 90
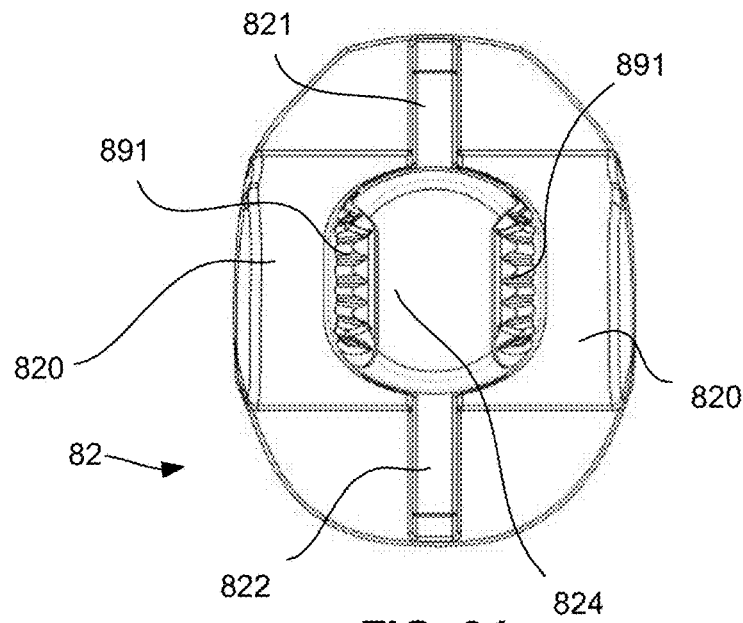
FIG. 91

REVERSE SHOULDER PROSTHESES WITH ANTI-ROTATION FEATURES

CROSS-REFERENCE TO RELATED APPLICATIONS

This application is a continuation if U.S. Patent Application No. 14/265,284, filed on Apr. 29, 2014, which is a continuation of PCT/EP2012/071618, filed on Oct. 31, 2012, which claims the benefit of U.S. Provisional Patent Application Ser. No. 61/553,720, filed on Oct. 31, 2011, of the European Patent Applications 11306725.0, 11306724.3, 11306727.6 and 11306728.4 filed on Dec. 21, 2011, and of U.S. Provisional Patent Application Ser. No. 61/596,148, filed on Feb. 7, 2012, all of which are incorporated by reference herein in their entireties for all purposes.

TECHNICAL FIELD

Embodiments of the present invention relate generally to prostheses, and more specifically to systems and methods for reverse and anatomic shoulder prostheses.

BACKGROUND

Arthroplasty is the standard of care for the treatment of shoulder joint arthritis. A typical humeral head replacement which attempts to mimic anatomic conditions involves a metallic humeral stem and a modular head replacement, capable of multiple positions for optimal boney coverage. Such humeral head replacement articulates with an opposing glenoid resurfacing device, which may be manufactured from UHMWPE.

For more severe cases of shoulder arthritis, the standard treatment is a reverse reconstruction, which includes reversing the kinematics of the shoulder joint. This is performed by securing a semi-spherical metallic device to the glenoid, referred to as a glenosphere, and implanting a metallic humeral stem with a modular cavity, typically manufactured from ultra high molecular weight polyethylene (UHMWPE), capable of receiving the glenosphere. The metallic humeral stem is usually offered in one fixed orientation that does not provide any eccentric adjustability to allow for proper fill in the humeral metaphysis.

As patient disease may progress after anatomic treatment, revision surgery may be necessary to perform a reverse reconstruction of the shoulder. Removal of anatomic devices that have integrated into the patient's boney anatomy proves to be difficult for the surgeon, and could potentially cause excessive patient bone loss.

Stems for shoulder prostheses typically permit a variety of neck angles to accommodate differing patient anatomies; such neck angles may range from 125 to 140 degrees, for example. Such stems are typically monoblock, which requires a separate stem implant component to be provided in a surgical kit for each neck angle, as well as each neck angle for each stem length option provided. This results in a large amount of inventory and thus design constraints on the number of angles that may be added to the implant range and/or provided by a single prosthesis surgical kit.

The anatomical neck of the humerus may be resected anywhere within a predetermined angle range, but the resultant angle is measured and the "closest" angle stem may be selected. This may result in minor non-conformities that are either not addressed (which may result in sub-optimal implant support and imaging) or corrected with secondary reaming (which may require an extra step and more time for the patient in the operating room). In addition, multiple monoblock stems provided in a surgical prosthesis may also require multiple trial implants to determine if the chosen neck angle is sufficient. Stem trialing often involves the insertion and removal of a part in the prepared humerus, which may potentially compromise the fit with the final implant in the humerus. This also adds an additional operating step, thereby increasing surgical time and exposure to anesthesia.

SUMMARY

A modular reverse shoulder prosthesis according to embodiments of the present invention includes a stem having a proximal taper and a primary stem axis, the proximal taper extending from the stem about a metaphyseal axis, the metaphyseal axis at an angle with respect to the primary stem axis, and a metaphysis having a proximal end, a distal end, a first aperture in the distal end configured to be placed over the proximal taper, and a second aperture in the proximal end having an insert axis that is eccentrically offset from the metaphyseal axis, the metaphysis configured for attachment to the stem at any rotational position of the metaphysis about the metaphyseal axis. Such a modular reverse shoulder prosthesis may be further configured for attachment to the stem at any rotational position selected from a three hundred sixty degree set of possible rotational positions of the metaphysis about the metaphyseal axis.

A modular reverse shoulder prosthesis according to embodiments of the present invention includes a stem having a proximal taper and a primary stem axis, the proximal taper extending from the stem about a metaphyseal axis, the metaphyseal axis at an angle with respect to the primary stem axis, a metaphysis having a proximal end, a distal end, a first aperture in the distal end configured to be placed over the proximal taper, and a second aperture in the proximal end having an insert axis that is eccentrically offset from the metaphyseal axis, the metaphysis configured for attachment to the stem at any rotational position of the metaphysis about the metaphyseal axis, and a reverse insert, the reverse insert having a proximal end and a distal end, wherein the proximal end comprises a concave cup formed about a cup axis and configured to receive a glenosphere, and wherein the distal end comprises a locking protrusion, wherein the locking protrusion has an outer surface with a cross-sectional shape that is rotationally symmetrical about the insert axis with respect to a corresponding inner surface of the second aperture, wherein the rotational symmetry has an order of six, seven, eight, nine, or ten. In some cases, the reverse insert is a flat insert for which the cup axis is substantially aligned with the insert axis. In other cases, the reverse insert is an angled insert for which the cup axis is at an angle with respect to the insert axis, such that the reverse insert is configured to lock with the metaphysis in at least six different positions, wherein the cup axis has a different radial orientation with respect to the metaphyseal axis at each of the at least six different positions. In yet other cases, the reverse insert is a flat insert for which the cup axis is offset from the insert axis.

The rotational symmetry may have an order of six, seven, eight, nine, or ten; in some cases, the rotational symmetry may have an order of eight. The cross-sectional shape may be octagonal, and the locking protrusion may include a locking lip, and wherein the inner surface of the second aperture may include a groove to engage with the locking lip. Such a locking lip may extend around an outer perimeter of the locking protrusion, and the groove may extend around an inner perimeter of the second aperture.

A modular reverse shoulder prosthesis according to embodiments of the present invention includes a stem having a proximal taper and a primary stem axis, the proximal taper extending from the stem about a metaphyseal axis, the metaphyseal axis at an angle with respect to the primary stem axis, the stem further comprising a proximal perimeter and a concavity formed between the proximal taper and the proximal perimeter, and a metaphysis having a proximal end, a distal end, a first aperture in the distal end configured to be placed over the proximal taper, and a second aperture in the proximal end having an insert axis that is eccentrically offset from the metaphyseal axis, the distal end having a distalmost end comprising a convex curvature, wherein the distalmost end is configured to engage the concavity of the stem when the metaphysis is attached to the stem, such that in an x-ray image in a coronal plane and/or in any other plane of the metaphysis attached to the stem, the proximal perimeter of the stem covers the distalmost end of the metaphysis. The metaphysis may be configured for attachment to the stem at any rotational position of the metaphysis about the metaphyseal axis, and the distalmost end may be configured to engage the concavity of the stem when the metaphysis is attached to the stem, such that in an x-ray image in a coronal plane of the metaphysis attached to the stem in any rotational position, the proximal perimeter of the stem covers the distalmost end of the metaphysis.

A modular reverse shoulder prosthesis according to embodiments of the present invention includes a stem and a metaphysis, the metaphysis configured for attachment to the stem along a modular interface, the stem and the metaphysis implanted into bone, wherein the modular interface is entirely set within the bone. This may permit conversion of the prosthesis from an anatomic configuration to a reverse configuration below the resection plane, according to embodiments of the present invention.

A method for implanting a modular reverse shoulder prosthesis having a stem and a metaphysis according to embodiments of the present invention includes implanting the stem into a bone, attaching the metaphysis to the stem along a modular interface, and setting the modular interface entirely within the bone.

A method for reaming a bone for implantation of a metaphysis according to embodiments of the present invention, wherein a stem with a proximal taper has already been implanted into the bone, the proximal taper having a metaphyseal axis, includes attaching a reamer guide to the proximal taper, the reamer guide having a distal reamer guide portion and a proximal reamer guide portion, the distal reamer guide portion having a distal reamer guide axis, the proximal reamer guide portion having a proximal reamer guide axis that is parallel to and offset from the distal reamer guide axis, rotating the reamer guide with respect to proximal taper about the metaphyseal axis to a desired angular orientation of the reamer guide, locking the reamer guide to the proximal taper at the desired angular orientation, reaming the bone with a first reamer that rotates about the distal reamer guide axis using the distal reamer guide to guide the first reamer, and reaming the bone with a second reamer that rotates about the proximal reamer guide axis using the proximal reamer guide to guide the second reamer. The proximal and distal reamer guide portions may be formed as a single piece. Such methods may further include inserting an offset indicator over the reamer guide such that the offset indicator and the reamer guide rotate as one about the metaphyseal axis, the offset indicator comprising an angle indicator, wherein rotating the reamer guide with respect to the proximal taper about the metaphyseal axis comprises rotating the offset indicator, the method further including using the angle indicator to mark the desired angular orientation.

A bone reamer according to embodiments of the present invention includes a distal reamer guide portion having a distal reamer guide axis, and a proximal reamer guide portion having a proximal reamer guide axis that is parallel to and offset from the distal reamer guide axis, wherein the distal reamer guide portion and proximal reamer guide portion are formed as a single piece. In some embodiments, the distal reamer guide portion has a cylindrical outer surface, and the proximal reamer guide portion has a crescent-shaped outer surface with a major diameter smaller than that of the cylindrical outer surface of the distal reamer guide portion. The bone reamer may include a distal end and a proximal end, and may further include a hole formed through the bone reamer from the distal end to the proximal end. According to some embodiments, the distal reamer guide completely encircles the hole, and the proximal reamer guide only partially encircles the hole.

A method for converting a modular anatomic shoulder implant to a modular reverse shoulder implant according to embodiments of the present invention, wherein the modular anatomic shoulder implant includes a distal stem, an anatomic metaphysis, and an anatomic humeral head, and wherein the modular reverse shoulder implant includes the distal stem, a reverse metaphysis, and a reverse insert, includes removing the anatomic humeral head from the anatomic metaphysis, separating the anatomic metaphysis from the distal stem, installing a reamer guide to the distal stem, reaming bone using the reamer guide to guide a reamer, attaching the reverse metaphysis to the distal stem at one of an unlimited number of rotational positions and setting the reverse metaphysis into the bone, and attaching the reverse insert to the reverse metaphysis in one of a fixed number of positions, the fixed number of positions corresponding to an order of rotational symmetry of the reverse insert distal end protrusion shape with respect to the reverse metaphysis proximal end opening shape. This process may be conducted using the same resection surface prepared for the modular anatomic shoulder implant procedure. In the case where the anatomic implant includes only a stem and a proximal head portion (which includes a metaphyseal portion and a head, for example as one piece), such a one-piece proximal head portion may be removed from the anatomic stem prior to installing the reamer guide to the stem, according to embodiments of the present invention. The interface of such a one-piece proximal head portion with the stem may be below the bone resection surface, according to embodiments of the present invention.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 32 illustrates a front elevation view of a reverse metaphysis in a first rotated position with respect to the distal stem, according to embodiments of the present invention.

FIG. 33 illustrates a front elevation view of the reverse metaphysis of FIG. 32 in a second rotated position with respect to the distal stem, according to embodiments of the present invention.

FIG. 34 illustrates a front elevation view of the reverse metaphysis of FIG. 32 in a third rotated position with respect to the distal stem, according to embodiments of the present invention.

FIG. 35 illustrates a front elevation view of the reverse metaphysis of FIG. 32 in a fourth rotated position with respect to the distal stem, according to embodiments of the present invention.

FIG. 36 illustrates a side elevation view of the reverse metaphysis and distal stem in the first rotated position of FIG. 32, according to embodiments of the present invention.

FIG. 37 illustrates a side elevation view of the reverse metaphysis and distal stem in the third rotated position of FIG. 34, according to embodiments of the present invention.

FIG. 89 illustrates a medial perspective view of the distal stem portion of FIGS. 78-80, looking directly into the screw hole along axis A89 of FIG. 83, according to embodiments of the present invention.

FIG. 90 illustrates a bottom perspective view of the proximal stem portion of FIGS. 81 and 82, according to embodiments of the present invention.

FIG. 91 illustrates a bottom plan view of the proximal stem portion of FIG. 90, according to embodiments of the present invention.

Figure 1:
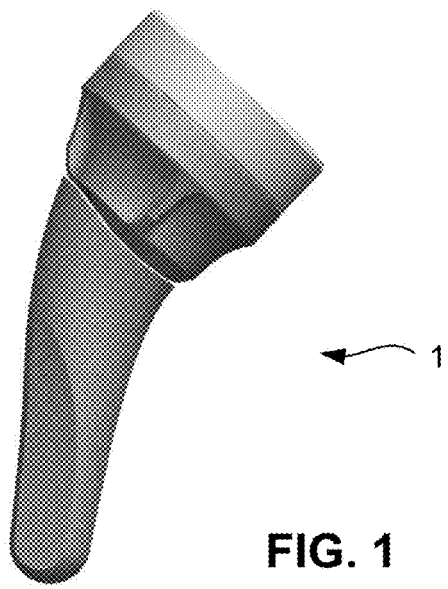
FIG. 1 illustrates a side elevation view of a modular reverse shoulder prosthesis, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
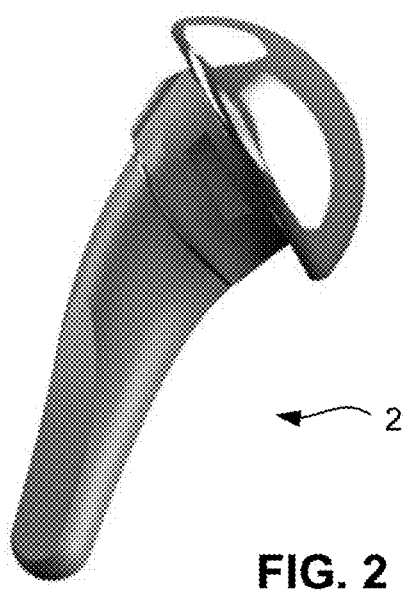
FIG. 2 illustrates a side elevation view of a modular anatomic shoulder prosthesis, according to embodiments of the present invention.
Figure 3:
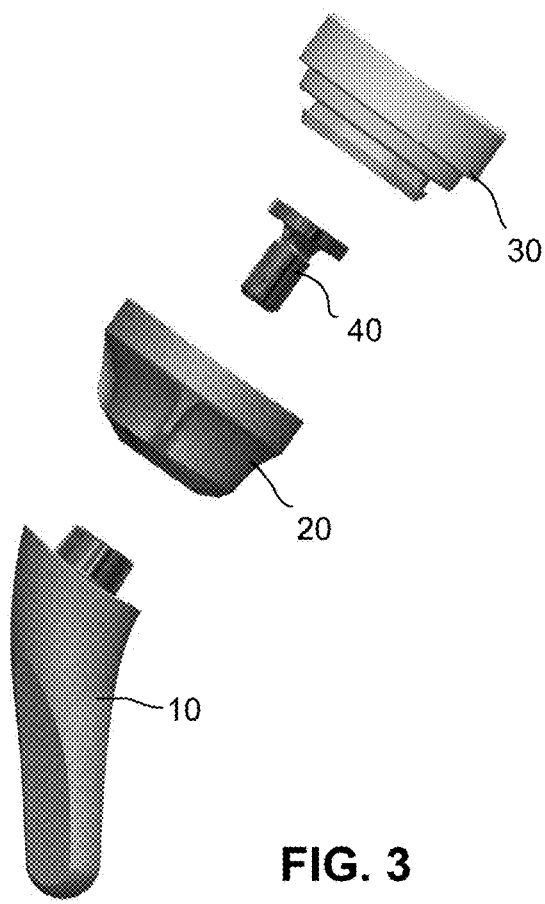
FIG. 3 illustrates an exploded view of the modular reverse shoulder prosthesis of FIG. 1, according to embodiments of the present invention.
Figure 4:
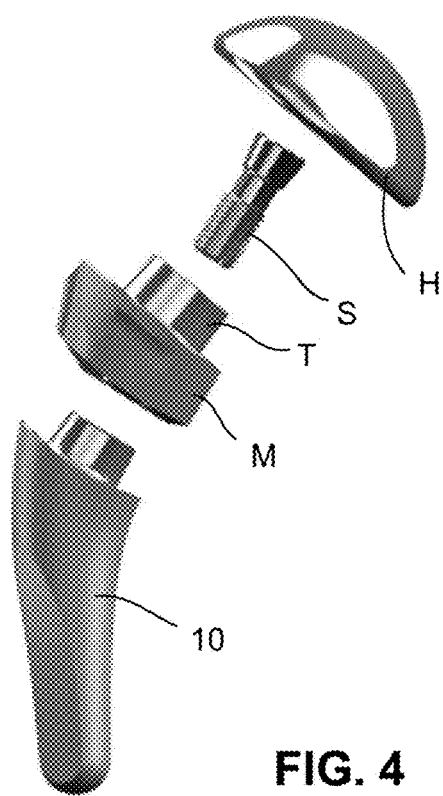
FIG. 4 illustrates an exploded view of the modular anatomic shoulder prosthesis of FIG. 2, according to embodiments of the present invention.
Figure 5:
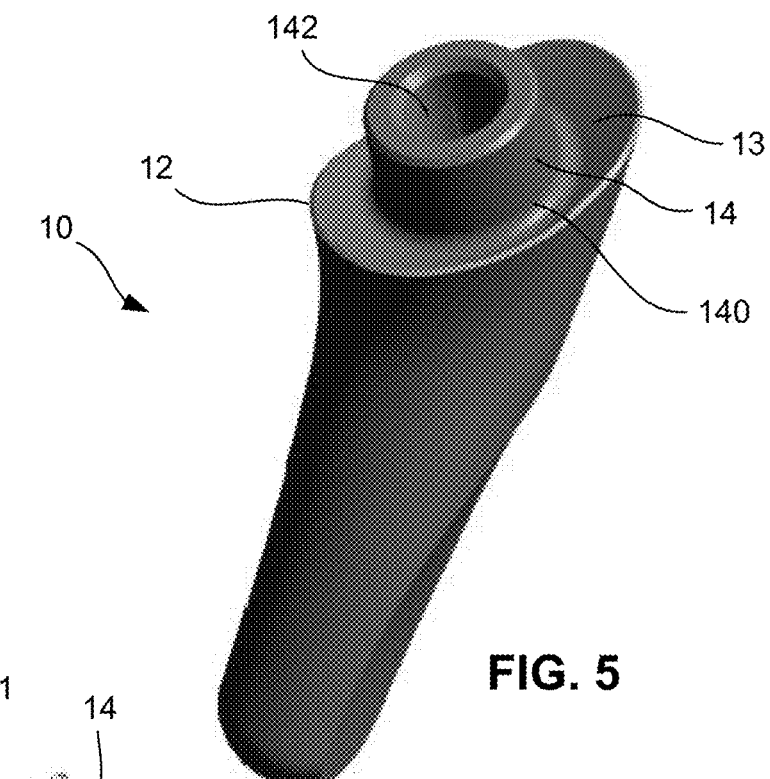
FIG. 5 illustrates a front perspective view of a distal stem component of the prostheses of FIGS. 1 to 4, according to embodiments of the present invention.
Figure 6:
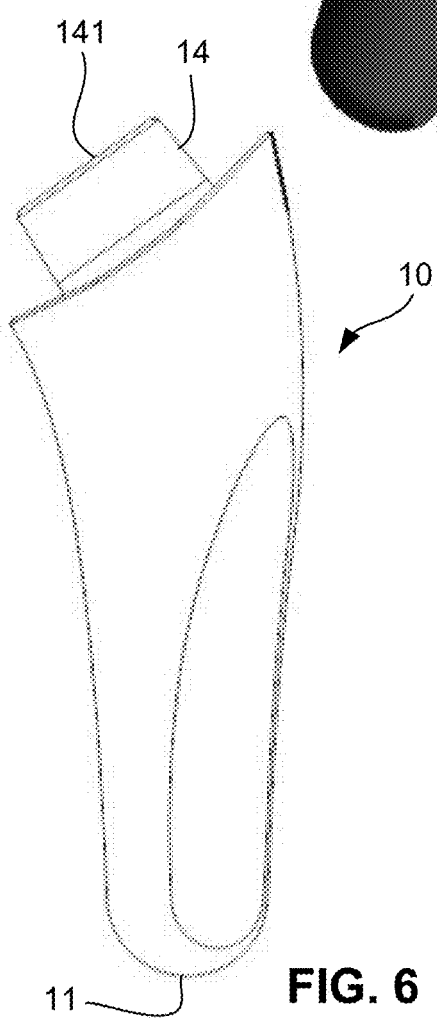
FIG. 6 illustrates a side elevation view of the distal stem of FIG. 5, according to embodiments of the present invention.
Figure 7:
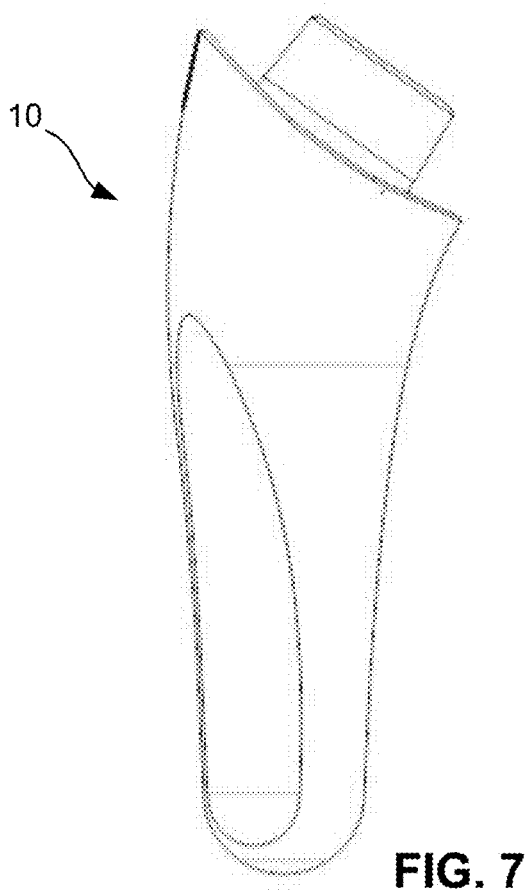
FIG. 7 illustrates another side elevation view of the distal stem of FIG. 5, according to embodiments of the present invention.
Figure 8:
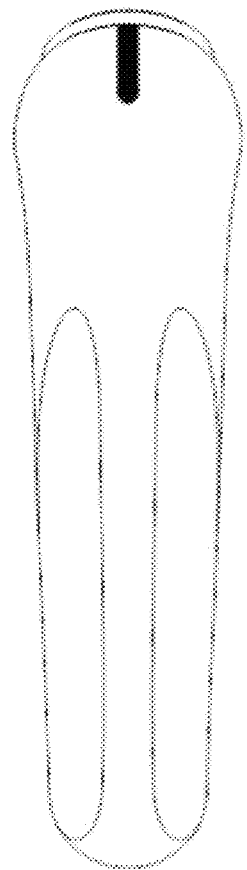
FIG. 8 illustrates a back elevation view of the distal stem of FIG. 5, according to embodiments of the present invention.
Figure 9:
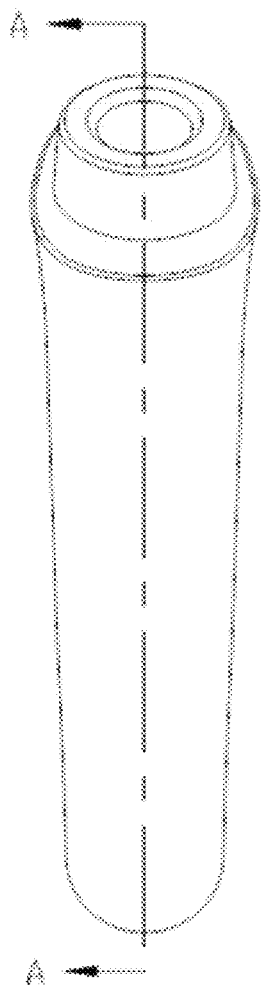
FIG. 9 illustrates a front elevation view of the distal stem of FIG. 5, according to embodiments of the present invention.
Figure 10:
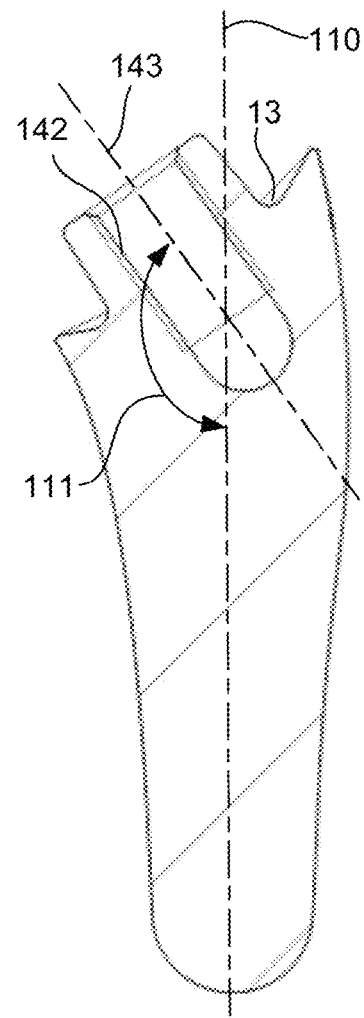
FIG. 10 illustrates a side cross-sectional view of the distal stem of FIG. 9, taken along line A-A of FIG. 9, according to embodiments of the present invention.
Figure 11A:
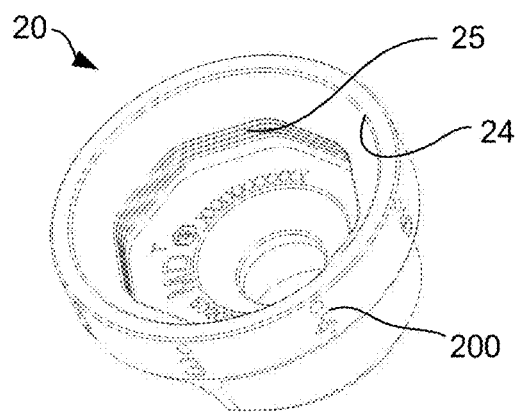
FIG. 11A illustrates a top perspective view of a metaphysis of a modular reverse shoulder prosthesis, according to embodiments of the present invention.

FIGS. 1 and 3 illustrate a modular reverse shoulder prosthesis 1, and FIGS. 2 and 4 illustrates a modular primary anatomic shoulder prosthesis 2, according to embodiments of the present invention. Reverse shoulder prosthesis 1 includes a distal stem 10, a reverse metaphysis 20, a reverse insert 30, and a modular screw 40 for coupling the reverse metaphysis 20 with the distal stem 10, according to embodiments of the present invention. Anatomic shoulder prosthesis 2 includes the same distal stem 10 (or may include another distal stem), a metaphysis M having a taper portion T, a screw S for coupling the metaphysis M with the distal stem 10, and an articular head H coupled to the proximal taper portion T of the metaphysis M, according to embodiments of the present invention.

FIGS. 5 to 10 illustrate the distal stem 10 in greater detail. Distal stem 10 includes a distal end 11, and a proximal taper 14 having a proximal end 141. The proximal taper 14 may include a hole 142, which may be threaded on its internal surface to engage with screw 40, according to embodiments of the present invention. Toward the proximal end 141, the stem 10 may also have a proximal perimeter 12 which extends around the taper 14, according to embodiments of the present invention. The stem 10 includes a concave portion 13 between the proximal perimeter 12 and the base 140 of the taper 14, according to embodiments of the present invention. This concave portion 13 forms a type of skirt, with the edge of the skirt corresponding to the proximal perimeter 12, according to embodiments of the present invention. As such, the base 140 of the taper 14 is not visible in either side view (of FIGS. 6 and 7). The stem 10 may have a gradually tapered overall shape in order to better fit the humerus bone into which it is implanted, according to embodiments of the present invention. The taper 14 may also have a tapered diameter which increases from the proximal end 141 toward the distal end 140.

FIGS. 11A to 19 illustrate the reverse metaphysis 20 in greater detail. Reverse metaphysis 20 includes a distal end 21 and a proximal end 22. The distal end 21 includes an opening 23 configured to interface with the proximal taper 14 of the distal stem 10; the inner taper angle of opening 23 corresponds to the outer taper angle of proximal taper 14, according to embodiments of the present invention. When metaphysis 20 is placed over the taper 14, the metaphyseal axis 29 substantially intersects the stem axis 143, according to embodiments of the present invention. The reverse metaphysis 20 also includes an opening 26 configured to receive the head 41 of the modular screw 40 (see FIGS. 29 and 46), as well as an octagonal opening 25 above the screw head opening 26, which may include one or more grooves 250. The grooves 250 may be formed by threading the inner surface of opening 25, according to embodiments of the present invention. The grooves 250 may extend around an entire inner perimeter of inner surface 25, according to embodiments of the present invention. The reverse metaphysis 20 may also include an opening 24 above opening 25, according to embodiments of the present invention. According to some embodiments of the present invention, opening 24 has a larger diameter than opening 25 which has a larger diameter than opening 26 which has a larger diameter than opening 23. Opening 23 may be in communication with opening 26 via another opening 230 of smaller diameter. The openings 23, 24, 25, 26, and 230 may all be in communication with one another, such that they together form one opening that extends from the proximal end 22 to the distal end 21 of reverse metaphysis 20, according to embodiments of the present invention.

Figure 15:
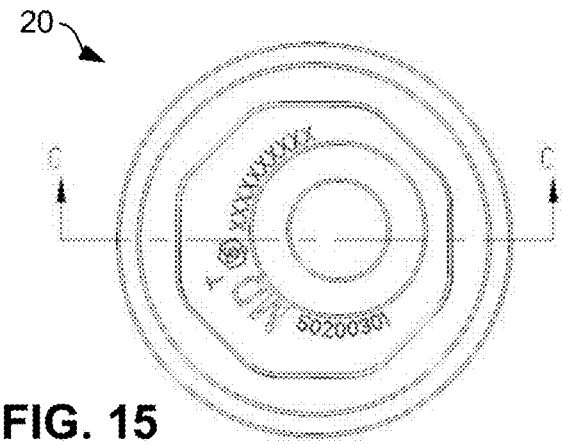
FIG. 15 illustrates another top perspective view of the metaphysis of FIG. 11A, according to embodiments of the present invention.
Figure 12:
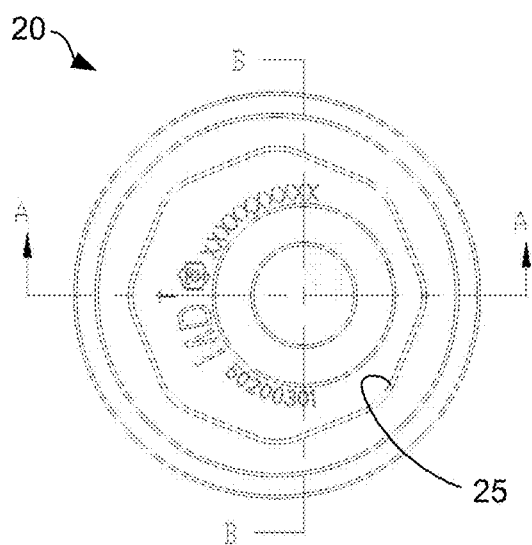
FIG. 12 illustrates a top plan view of the metaphysis of FIG. 11A, according to embodiments of the present invention.
Figure 16:
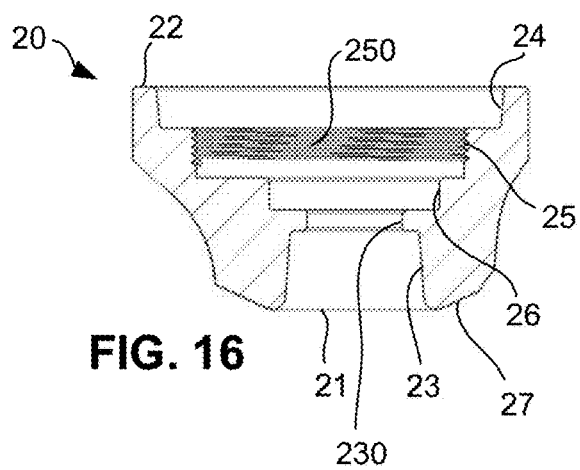
FIG. 16 illustrates a cross-sectional view of the metaphysis of FIG. 15, taken along line C-C of FIG. 15, according to embodiments of the present invention.
Figure 13:
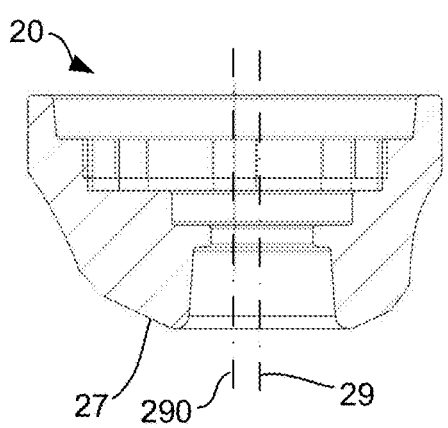
FIG. 13 illustrates a cross-sectional view of the metaphysis of FIG. 12, taken along line A-A of FIG. 12, according to embodiments of the present invention.
Figure 14:
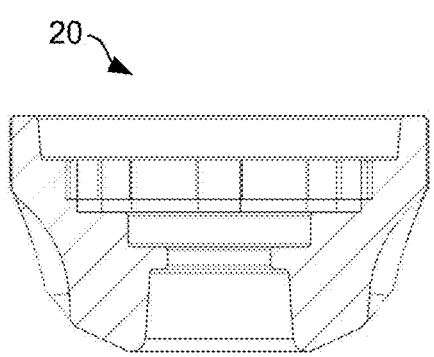
FIG. 14 illustrates a cross-sectional view of the metaphysis of FIG. 12, taken along line B-B of FIG. 12, according to embodiments of the present invention.
Figure 17:
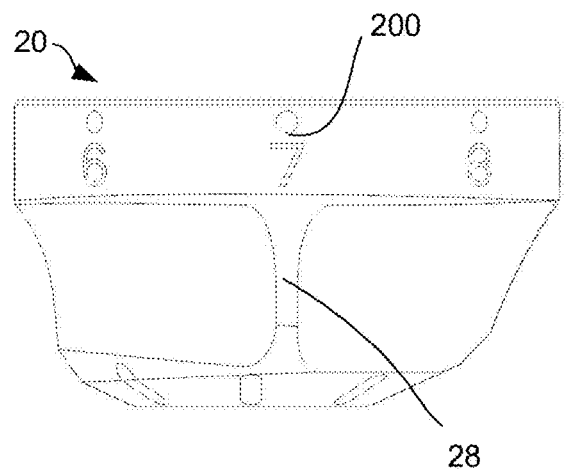
FIG. 17 illustrates a front elevation view of the metaphysis of FIG. 11A, according to embodiments of the present invention.
Figure 18:
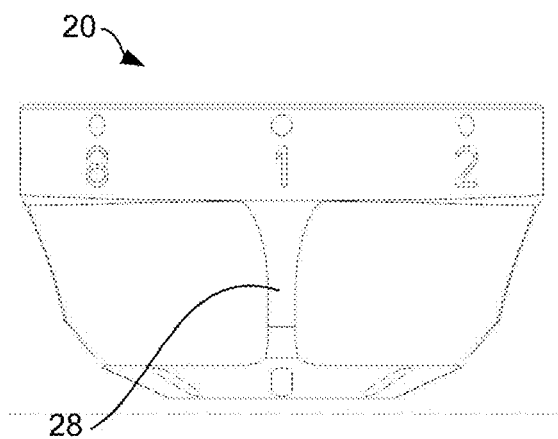
FIG. 18 illustrates a side elevation view of the metaphysis of FIG. 11A, according to embodiments of the present invention.
Figure 11B:
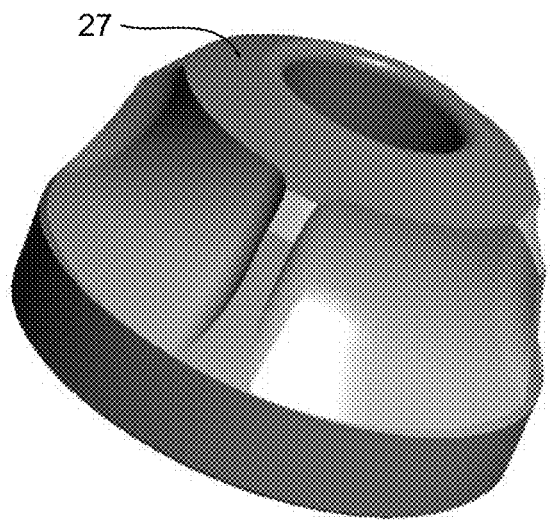
FIG. 11B illustrates a bottom perspective view of the metaphysis of FIG. 11A, according to embodiments of the present invention.
Figure 19:
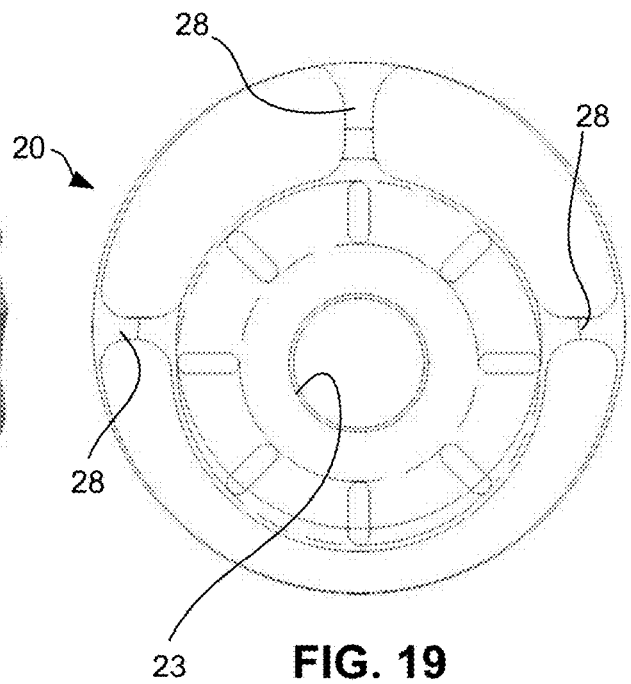
FIG. 19 illustrates a bottom plan view of the metaphysis of FIG. 11A, according to embodiments of the present invention.
Figure 20A:
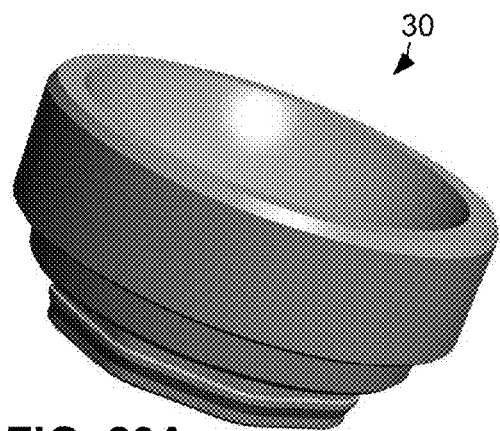
FIG. 20A illustrates a front perspective view of a reverse insert, according to embodiments of the present invention.
Figure 21:
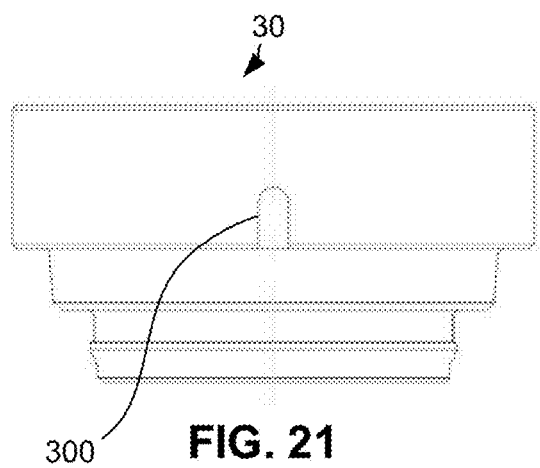
FIG. 21 illustrates a front elevation view of the reverse insert of FIG. 20A, according to embodiments of the present invention.
Figure 22:
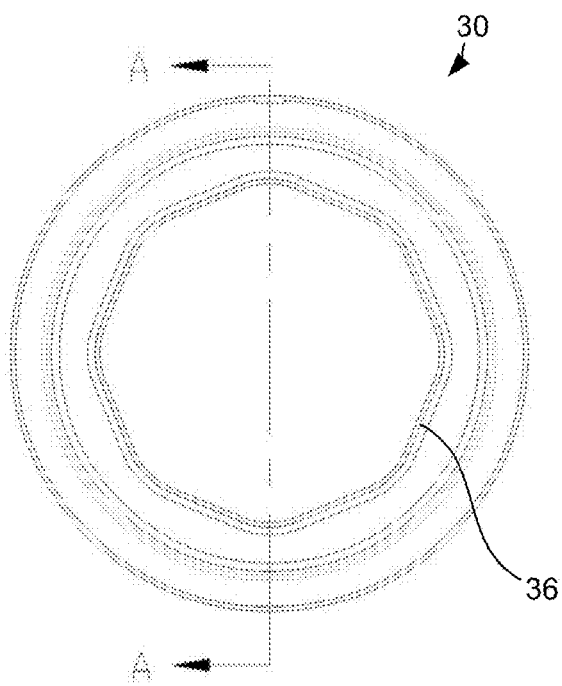
FIG. 22 illustrates a bottom plan view of the reverse insert of FIG. 20A, according to embodiments of the present invention.
Figure 23:
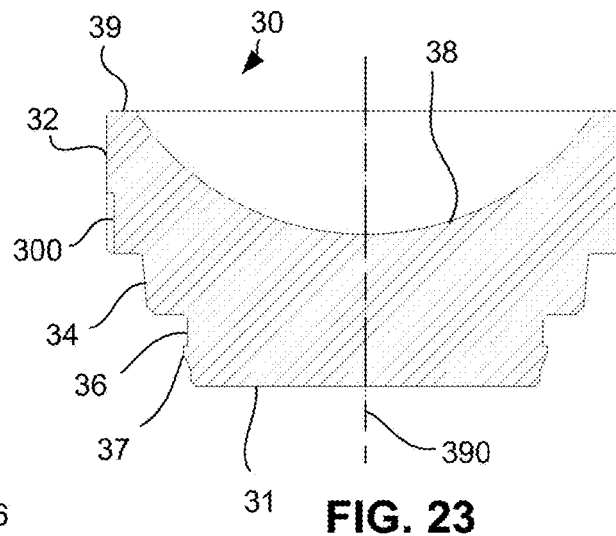
FIG. 23 illustrates a cross-sectional view of the reverse insert of FIG. 22, taken along line A-A of FIG. 22, according to embodiments of the present invention.
Figure 20B:
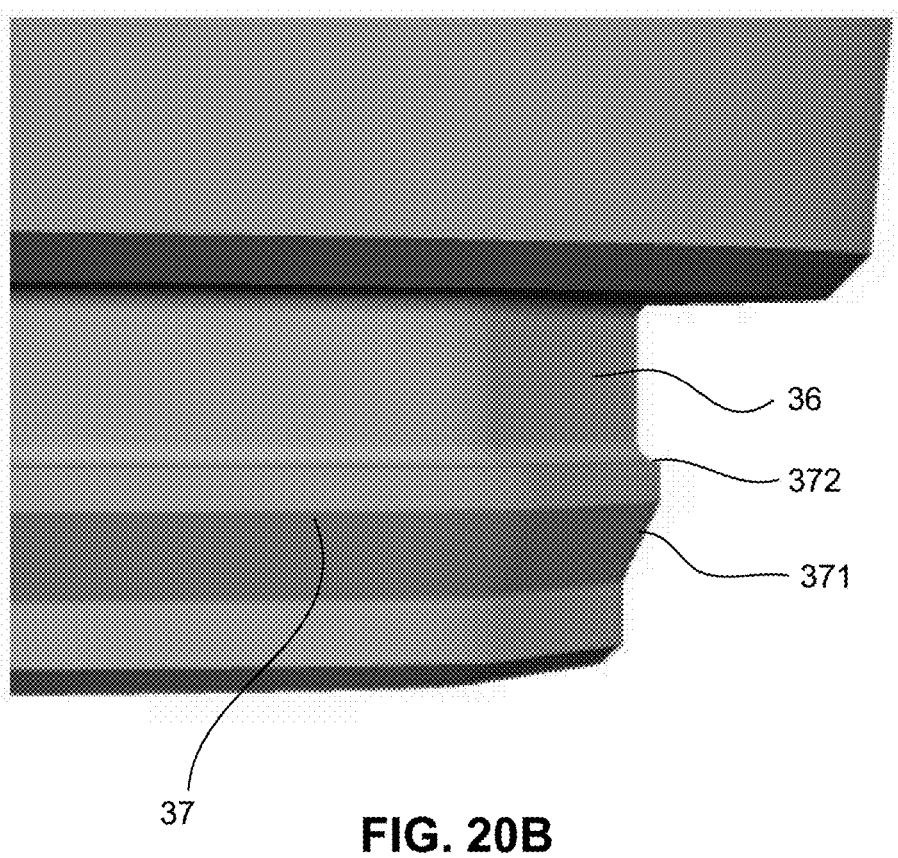
FIG. 20B illustrates an enlarged view of a locking lip of the reverse insert of FIG. 20A, according to embodiments of the present invention.
Figure 24:
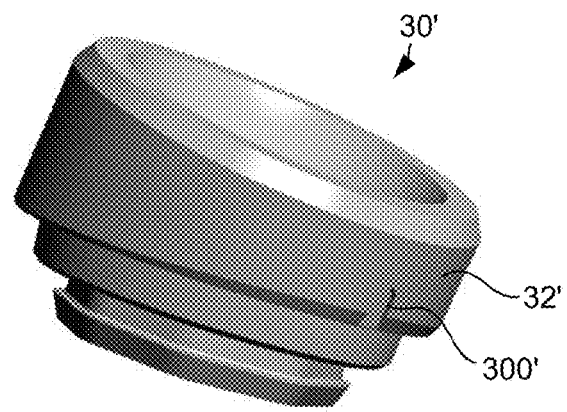
FIG. 24 illustrates a front perspective view of another reverse insert, according to embodiments of the present invention.
Figure 25:
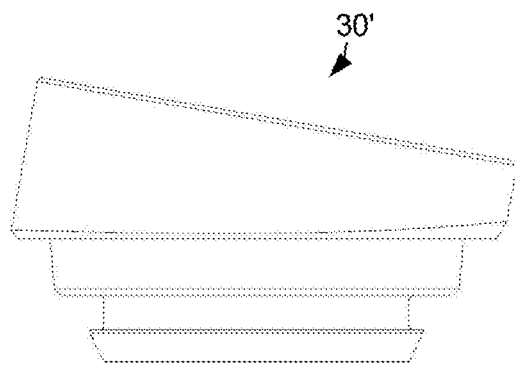
FIG. 25 illustrates a side elevation view of the reverse insert of FIG. 24, according to embodiments of the present invention.
Figure 26:
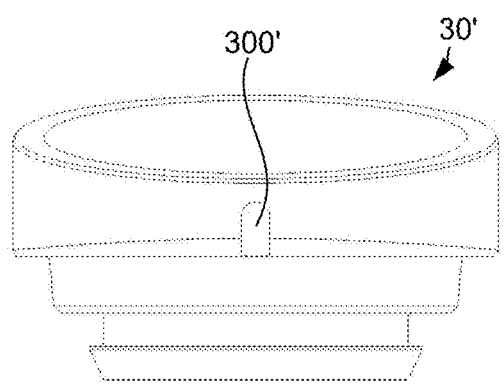
FIG. 26 illustrates a front elevation view of the reverse insert of FIG. 24, according to embodiments of the present invention.
Figure 27:
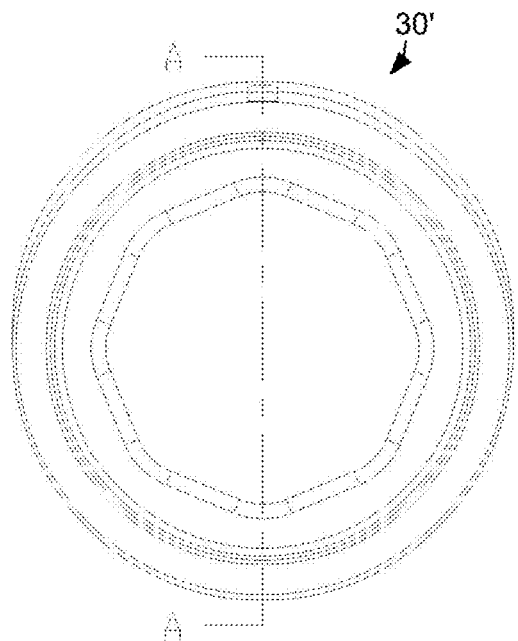
FIG. 27 illustrates a bottom plan view of the reverse insert of FIG. 24, according to embodiments of the present invention.
Figure 28:
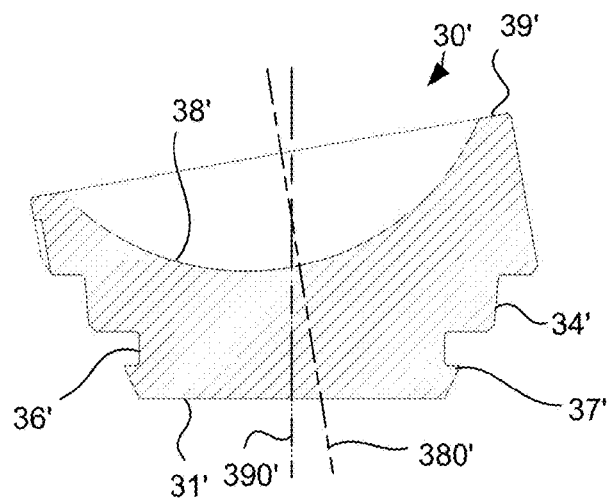
FIG. 28 illustrates a cross-sectional view of the reverse insert of FIG. 27, taken along line A-A of FIG. 27, according to embodiments of the present invention.

According to some embodiments of the present invention, the opening 25 may be octagonal in shape, as shown in FIGS. 12 and 15. The center of the octagonal shape of opening 25 intersects an axis 290, shown in FIG. 13. The center of openings 23, 26, and 230 intersects an axis 29, also shown in FIG. 13. Because opening 25 is configured to receive the locking mechanism of reverse insert 30, and because opening 23 is configured to interface with the proximal taper 14 of stem 10, and because axes 290 and 29 are offset from one another, the reverse metaphysis permits eccentric dialing.

Near its distal end 21, the reverse metaphysis 20 includes a curved surface 27, which may be substantially convex in shape, and may be configured to conform at least partially with the concavity 13 of the stem 10 when the metaphysis 20 is placed onto the stem 10. These at least partially matching surfaces 13, 27 permit the metaphysis 20 to be rotated about axis 29 with respect to the stem 10 to any position within 360 degrees of rotation, while permitting the maintenance of contact between surfaces 13, 27, according to embodiments of the present invention. The reverse metaphysis may also include one or more stabilization fins 28 configured to deter rotation of the metaphysis 20 with respect to the stem 10 once a rotational position of the metaphysis 20 has been selected and the metaphysis 20 implanted, according to embodiments of the present invention. Finally, the metaphysis 20 may also include visual markings 200, for example radially graduated markings and/or numbers, for example at eight equally-spaced radial positions, in order to assist the surgeon in indexing a relative position of the metaphysis 20, either with respect to the stem 10, and/or with respect to the insert 30, according to embodiments of the present invention. According to some embodiments of the present invention, the visual markings 200 include eight position markers and the numbers one through eight, one at each equally spaced marker, to indicate the location at which the indexing marker 300 of an insert 30 should align such that the octagonal locking protrusion 36 is aligned with the octagonal opening 25 of the metaphysis 20.

According to some embodiments of the present invention, the visual markings 200 include eight position markers and the numbers one through eight, one at each equally spaced marker, to indicate the location at which the indexing marker 300' of an angled insert 30' should align such that the octagonal locking protrusion 36' is aligned with the octagonal opening 25 of the metaphysis 20.

FIGS. 20A to 23 illustrate a reverse insert 30, according to embodiments of the present invention. Insert 30 may include a distal end 31 and a proximal end 39. The proximal end 39 may include a concave surface 38 configured to interface with a glenosphere or the like implanted in the patient's glenoid as part of the reverse prosthesis surgery. The insert 30 may include an outer wall 32 which is substantially cylindrical. Insert 30 may further include an octagonal locking protrusion 36 at its distal end 31, which is configured to interface with and pressure fit with the octagonal opening 25 of the metaphysis 20, according to embodiments of the present invention.

The locking protrusion 36 may include one or more locking lips 37 configured to engage with the one or more grooves 250 in opening 25 of the reverse metaphysis 20, according to embodiments of the present invention. The locking lip 37 may extend around an entire outer periphery of the octagonal locking protrusion 36, according to embodiments of the present invention. The locking lip 37 may include a gradually ramped portion 371 toward distal end 31, and a perpendicular or right-angle stop portion 372 toward the proximal end 39 of the locking lip 37 (see FIG. 20B), according to embodiments of the present invention. This permits locking lip 37 to slide into and over one or more grooves 250, while deterring the disengagement of the lip 37 from the groove 250 when a force is exerted on the insert 30 in the opposite direction, according to embodiments of the present invention. According to embodiments of the present invention, the top 372 of the lip 37 is similar to a tooth which grips and/or digs into the one or more grooves 250 to better secure the insert 30 within the metaphysis 20.

Because the insert 30 is radially symmetric about axis 390, and because the octagonal cross-sectional shape of locking protrusion 36 is configured to mate with the octagonal shape of opening 25, the insert 30 may be impacted into any of eight locked positions with respect to the metaphysis 20. However, because the insert 30 is a flat insert, not an angled insert like insert 30', the rotational position of the insert 30 about axis 390 (see FIG. 23) does not change the performance or operative geometry of the implant 1. The insert 30 may further include a ledge 34 above the locking protrusion 36 and below the cup 38; ledge 34 may be configured to interface with opening 24 on metaphysis 20; ledge 34 may also have an outer surface that is tapered, according to embodiments of the present invention.

FIGS. 24-28, on the other hand, show an insert 30' which is angled. Although one particular insert 30' is shown with one particular angle of ten degrees, other inserts having other angles may be used. Insert 30' may include a distal end 31' and a proximal end 39'. The proximal end 39' may include a concave surface 38' configured to interface with a glenosphere or the like implanted in the patient's glenoid as part of the reverse prosthesis surgery. The insert 30' may include an outer wall 32' which is substantially cylindrical. Insert 30' may further include an octagonal locking protrusion 36' at its distal end 31', which is configured to interface with and pressure fit with the octagonal opening 25 of the metaphysis 20, according to embodiments of the present invention. The locking protrusion 36' may include one or more locking lips 37' configured to engage with the one or more grooves 250 in opening 25 of the reverse metaphysis 20, according to embodiments of the present invention. The locking lip 37' may extend around an entire outer periphery of the octagonal locking protrusion 36', according to embodiments of the present invention. The locking lip 37' may include a gradually ramped portion toward distal end 31', and a perpendicular or right-angle stop portion toward the proximal end 39' of the locking lip 37', according to embodiments of the present invention. This permits locking lip 37' to slide into and over one or more grooves 250, while deterring the disengagement of the lip 37' from the groove 250 when a force is exerted on the insert 30' in the opposite direction, according to embodiments of the present invention. According to embodiments of the present invention, the top of the lip 37' is similar to a tooth which grips and/or digs into the one or more grooves 250 to better secure the insert 30' within the metaphysis 20.

Because the locking protrusion 36' of insert 30' is radially symmetric about axis 390', and because the octagonal cross-sectional shape of locking protrusion 36' is configured to mate with the octagonal shape of opening 25, the insert 30' may be impacted into any of eight locked positions with respect to the metaphysis 20. Because the insert 30' is an angled insert, rotating the insert 30' about axis 390' (e.g. between one of eight positions) changes the directional orientation of the cup axis 380' with respect to the metaphysis 20, according to embodiments of the present invention. Axis 390' may be an axial centerline of the spherical concave portion 38', according to embodiments of the present invention. The insert 30' may further include a ledge 34' above the locking protrusion 36' and below the cup 38'; ledge 34' may be configured to interface with opening 24 on metaphysis 20; ledge 34' may also have an outer surface that is tapered, according to embodiments of the present invention. Reverse inserts 30, 30' may be made of ultra high molecular weight polyethylene (UHMWPE), according to embodiments of the present invention. The stem 10 and/or metaphysis 20 may be made of biocompatible metal, for example titanium, according to embodiments of the present invention.

Figure 29:
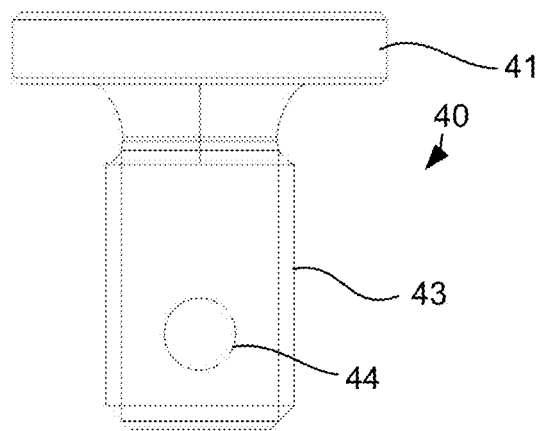
FIG. 29 illustrates a front elevation view of a modular assembly screw, according to embodiments of the present invention.
Figure 30:
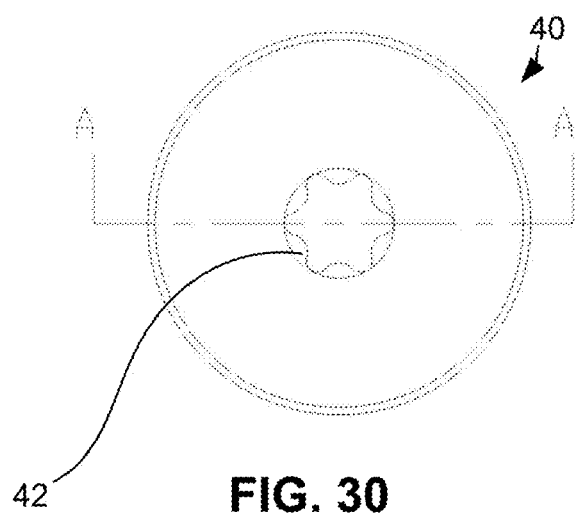
FIG. 30 illustrates a top plan view of the screw of FIG. 29, according to embodiments of the present invention.
Figure 31:
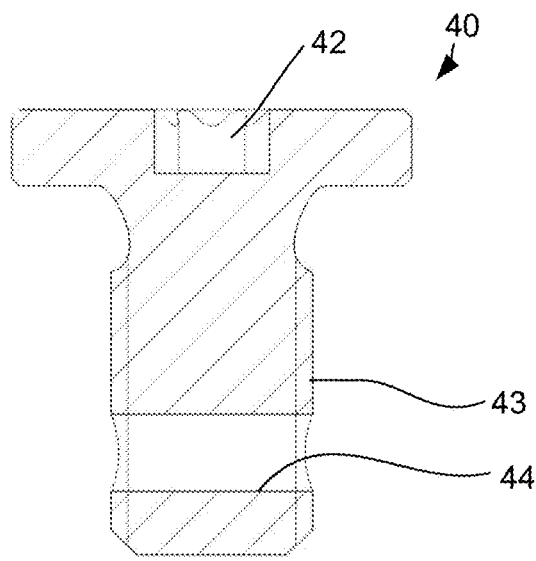
FIG. 31 illustrates a cross-sectional view of the screw of FIG. 30, taken along line A-A of FIG. 30, according to embodiments of the present invention.
Figure 38:
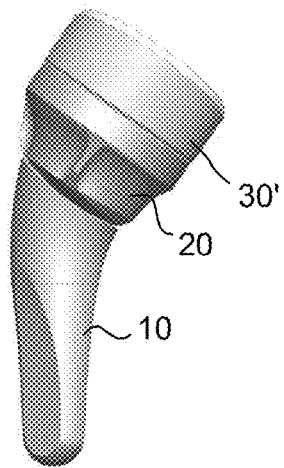
FIG. 38 illustrates a side elevation view of a modular reverse shoulder prosthesis with the reverse insert in a first rotational position with respect to the metaphysis, according to embodiments of the present invention.
Figure 40:
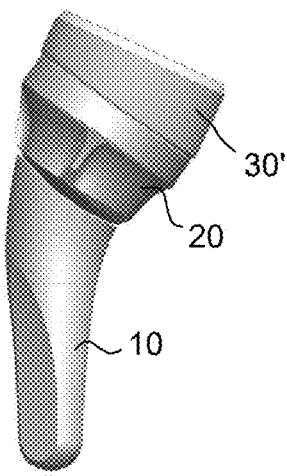
FIG. 40 illustrates a side elevation view of the modular reverse shoulder prosthesis of FIG. 38 with the reverse insert in a second rotational position with respect to the metaphysis, according to embodiments of the present invention.
Figure 42:
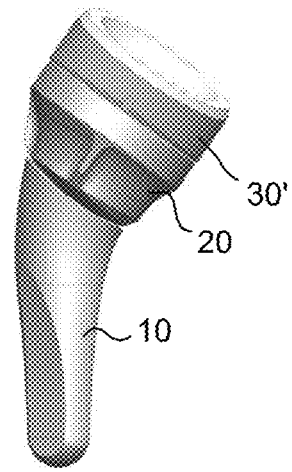
FIG. 42 illustrates a side elevation view of the modular reverse shoulder prosthesis of FIG. 38 with the reverse insert in a third rotational position with respect to the metaphysis, according to embodiments of the present invention.
Figure 39:
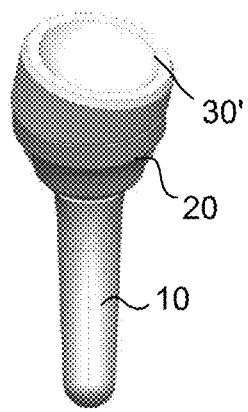
FIG. 39 illustrates a front elevation view of the modular reverse shoulder prosthesis in the position of FIG. 38, according to embodiments of the present invention.
Figure 41:
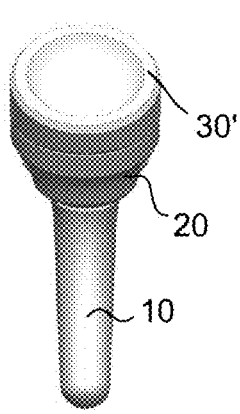
FIG. 41 illustrates a front elevation view of the modular reverse shoulder prosthesis in the position of FIG. 40, according to embodiments of the present invention.
Figure 43:
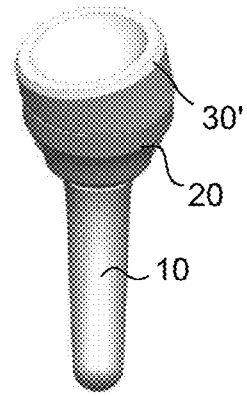
FIG. 43 illustrates a front elevation view of the modular reverse shoulder prosthesis in the position of FIG. 42, according to embodiments of the present invention.

FIGS. 29 to 31 illustrate a modular screw 40, according to embodiments of the present invention. Screw 40 includes a head portion 41 and a shaft portion 43, according to embodiments of the present invention. The head portion 41 may include a driver interface 42 configured to receive an operational end of a screw driver, according to embodiments of the present invention. The shaft portion 43 may be all or partially threaded, in order to threadably engage the opening 142 of stem 10, according to embodiments of the present invention. The shaft portion 43 may also include a through-hole 44. Through-hole 44 may be configured to receive a thread locking material, for example a polymer and/or adhesive material configured to strengthen and secure the interface of screw 40 and hole 142 and to deter loosening of the screw 40, according to embodiments of the present invention.

FIGS. 32 to 37 illustrate four possible positions of the metaphysis 20 with respect to the stem 10. FIGS. 32 and 36 illustrate the metaphysis 20 in the position corresponding to the furthest proximal placement of the insert axis 290 eccentricity; FIGS. 34 and 37 illustrates the metaphysis 20 in the position corresponding to the furthest distal placement of the insert axis 290 eccentricity; and FIGS. 33 and 35 illustrate side placements of the insert axis 290 with respect to the stem axis 143/metaphyseal axis 29. Although four distinct positions are shown, the metaphysis 20 may be attached to the stem 10 at any rotational position about axis 29, including three hundred sixty degrees of rotational freedom prior to attachment. In other words, there are an infinite or unlimited number of rotational positions of the metaphysis 20 about axis 29 with respect to the stem 10 that may be implemented prior to attachment of the metaphysis 20 to the stem 10, according to embodiments of the present invention. The surgeon may select the preferred rotational position based on one or more factors; for example, the surgeon may select the rotational position of the metaphysis 20 with respect to the stem 10 which corresponds to the best fit with the surrounding bone. This may be done to maximize the thickness of the bone surrounding the metaphysis 20, for example.

According to some embodiments of the present invention, this rotational relationship of the metaphysis 20 with respect to the stem prior to fixation may be referred to as "infinite dialability," referring to the fact that a surgeon may "dial" (e.g. turn or rotate) any desired angle between the eccentricity of the metaphysis 20 and the stem axis 143, according to embodiments of the present invention. Although the freedom of movement and "dialability" of the metaphysis 20 with respect to the stem 10 is referred to as being rotational in nature, this refers to the freedom of movement but is not intended to imply that the metaphysis 20 would rotate with respect to the stem 10 or the surrounding bone after the metaphysis 20 is implanted, as the interface between the metaphysis 20 and the stem 10 is actually below the resection surface, according to embodiments of the present invention. As such, the metaphysis 20 is configured to be attached to the stem 10 at any rotational position about axis 29 or axis 143, according to embodiments of the present invention.

FIGS. 38 to 43 illustrate various positions in which the insert 30' may be interlocked with the metaphysis 20, according to embodiments of the present invention. Because insert 30' is angled, and because there are eight possible positions in which the insert 30' may be interlocked with the metaphysis 20, there are eight possible angles at which the cup 38' axis 380' may be oriented rotationally about the metaphysis 20, according to embodiments of the present invention. This permits the surgeon to select the best angle and placement for the cup 38' axis 380', according to embodiments of the present invention. Because the metaphysis itself 20 includes an eccentricity which may be customized or dialed with respect to the stem 10, and because the insert 30' includes an angular eccentricity which may be customized with respect to the metaphysis 20, and because other inserts may be provided which are "flat" or which have smaller or greater angular eccentricities, the modular reverse shoulder system 1 gives the surgeon a high degree of customizability for a particular patient, with a relatively small number of parts, according to embodiments of the present invention. As described above, marker 300' may be used to facilitate proper placement of the insert 30' with respect to metaphysis 20, and/or to help the surgeon remember the index position of a particular desired placement. Trial inserts may also be provided with a marker similar to marker 300' so the surgeon can recreate the trial condition with the actual insert 30', according to embodiments of the present invention.

The locking protrusion 36 and lip 37 of insert 30 serve as both a locking mechanism to hold the insert 30 securely to the metaphysis 20, and also an anti-rotation mechanism to prevent rotation of the insert 30 about insert axis 390 when the insert 30 has been engaged with metaphysis 20, according to embodiments of the present invention. The lip 37, which may have other cross-sectional profiles other than the barbed profile shown, and which may be continuous or intermittent about the outer perimeter of protrusion 36, serves to permit insertion of the protrusion 36 into opening 25, but also serves to deter inadvertent or unwanted release from the metaphysis 20 by grabbing onto (or becoming attached or anchored to) the grooves 250 in opening 25, according to embodiments of the present invention. Also, the overall pressure fit between metaphysis 20 and insert 30, which may be snug and which may be (but not necessarily) configured to occur only with the use of an impacting tool, contributes to the secure coupling of the two elements. According to some embodiments of the present invention, the locking protrusion 36 does not include lip 37, but instead relies on the pressure fit between insert 30 and metaphysis 20 to hold the two together. According to other embodiments of the present invention, additional or alternative structures are used to interlock the insert 30 with the metaphysis 20. Although insert 30 is described, the discussion herein regarding the locking protrusion 36 applies also to the locking protrusion 36' of insert 30', according to embodiments of the present invention.

The anti-rotation mechanism includes the polygonal interface between insert 30 and metaphysis 20. Although an octagonal interface is shown, one of ordinary skill in the art, based on the disclosure provided herein, will appreciate that anti-rotation interfaces of other cross-sectional shapes may be used. For example, a pentagon, hexagon, heptagon, octagon, nonagon, or decagon shape may be used. And although a polygon is shown having straight sides in the form of an octagon, one of ordinary skill in the art will appreciate, based on the disclosure provided herein, that other rotationally symmetric cross sectional shapes may be used for the locking protrusion 36, for example star shape, or a polygon with curved (inward or outward) or wavy or irregular sides. And although the insert 30 is shown as having a male locking protrusion 36 and metaphysis 20 as having a female opening 25 for receiving protrusion 36, the insert 30 may alternatively have a female opening, and the metaphysis 20 a male locking protrusion, according to embodiments of the present invention.

The number of possible rotational positions in which the insert 30 may be locked into the metaphysis 20 depends upon the order of the rotational symmetry of the cross-sectional shape of the locking protrusion 36 and opening 25. For example, an octagonal cross-sectional shape is shown, which has a rotational symmetry about axis 390 with an order of eight. According to some embodiments of the present invention, the order of rotational symmetry of the cross-sectional geometric shape of locking protrusion 36 and opening 25 is seven to nine. According to some embodiments of the present invention, the order of rotational symmetry of the cross-sectional geometric shape of locking protrusion 36 and opening 25 is six to ten. According to some embodiments of the present invention, the order of rotational symmetry of the cross-sectional geometric shape of locking protrusion 36 and opening 25 is five to eleven.

According to embodiments of the present invention, the polygonal or rotationally symmetrical cross sectional shape of the locking protrusion 36 and opening 25 also serve to deter undesired mismatch between the position of the insert 30 with respect to the metaphysis 20. According to embodiments of the present invention, the insert 30 does not permit locking of the insert 30 with the metaphysis 20 unless their respective shapes are properly aligned. As such, the insert 30 and metaphysis 20 interaction may be described as "self-aligning," resulting in a quick, attractive, and elegant assembly. Use of a male-female interface having a rotational symmetry between insert 30 and metaphysis 20 provides an elegant and easy-to-use mechanism for locking the insert 30 to the metaphysis 30 and for preventing rotation of the insert 30 with respect to the metaphysis, without the use of potentially unsightly and less stable smaller protrusions or teeth depending from either insert 30 or metaphysis 20, according to embodiments of the present invention. Embodiments of the present invention permit the independent customization of the position of the metaphysis 20 with respect to the stem 10, as well as the independent customization of the insert 30 with respect to the metaphysis 20. In existing humeral implants, the versioning, in other words the angle formed between the metaphysis and the stem with respect to a coronal plane, is typically twenty to forty degrees for an anatomical shoulder prosthesis, and is typically zero to twenty degrees for a reverse shoulder prosthesis. Thus, many surgeons choose a fixed version angle of twenty degrees when implanting a primary anatomical shoulder prosthesis, so that they do not have to remove the stem or the whole implant when performing a revision from anatomic to reverse. Embodiments of the present invention, however, permit a surgeon to perform the anatomic-to-reverse conversion while also customizing any desired version angle for both the anatomic shoulder and reverse shoulder, independently, and while using the same implanted stem 10.

Figure 44:
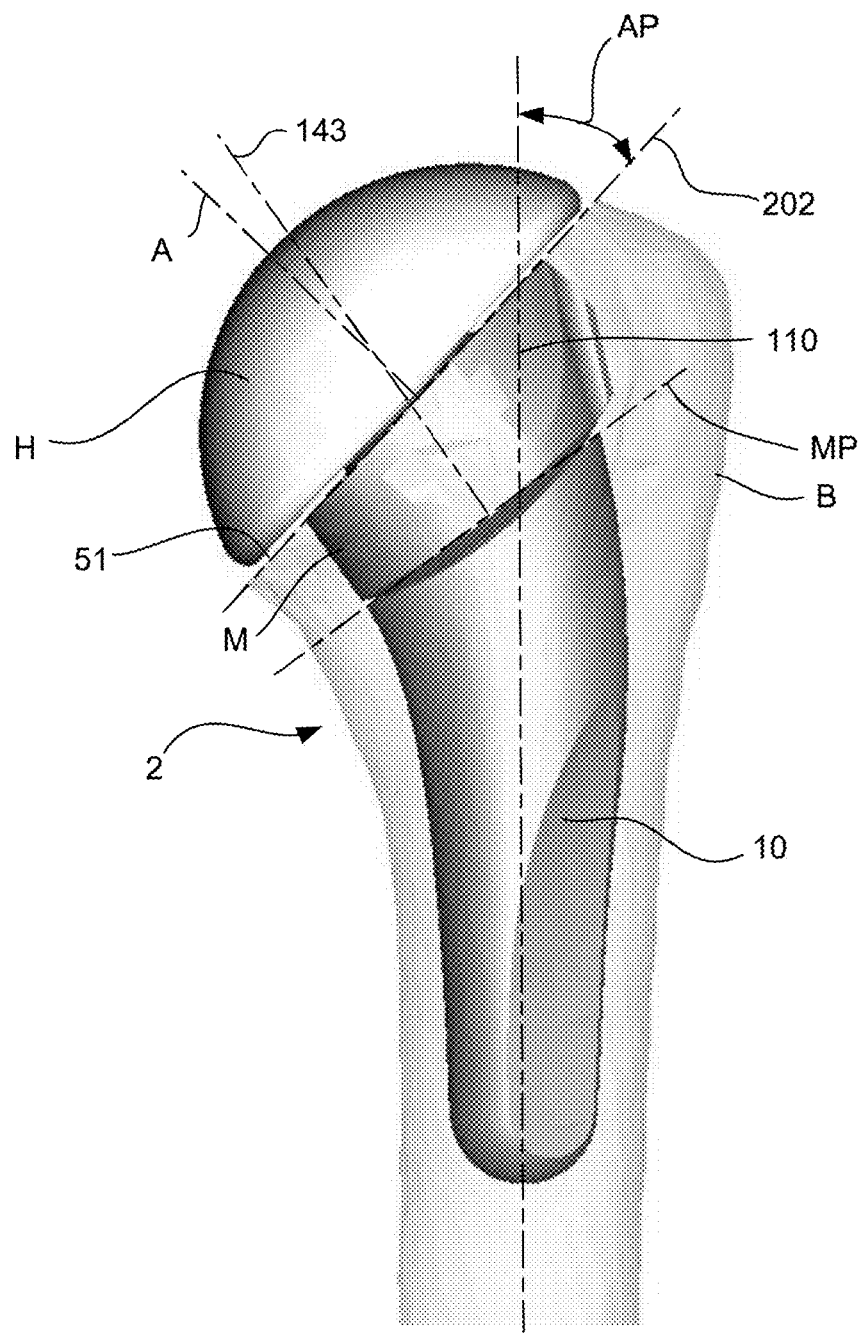
FIG. 44 illustrates a side elevation view of the modular anatomic shoulder prosthesis of FIG. 2 implanted into a bone, according to embodiments of the present invention.
Figures 45, 46:
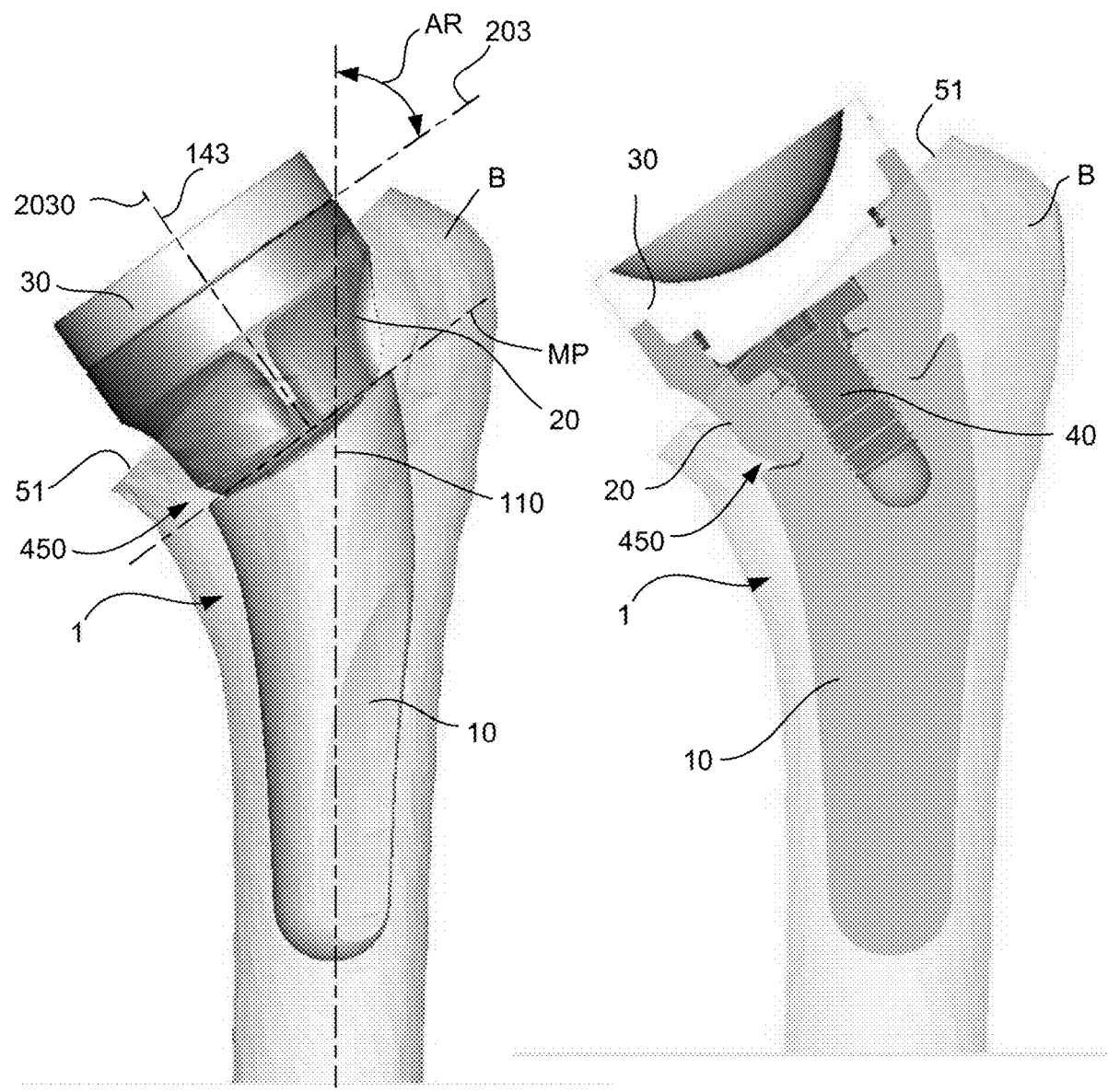
FIG. 45 illustrates a side elevation view of a modular reverse shoulder prosthesis that has been converted from a primary anatomic shoulder prosthesis, according to embodiments of the present invention.
FIG. 46 illustrates a side cross-sectional view of the modular reverse converted shoulder prosthesis of FIG. 45 implanted into the bone, according to embodiments of the present invention.

FIG. 44 illustrates a modular anatomic shoulder prosthesis 2 implanted in a bone B, according to embodiments of the present invention. The resection plane 51 may be substantially flush with the proximal surface of the metaphysis M, and the interface between the metaphysis M and stem 10 is below the resection surface 51, according to embodiments of the present invention. When a surgeon desires to convert a primary anatomic shoulder prosthesis into a reverse shoulder prosthesis, he must typically remove the entire prosthesis, thereby risking further weakening the bone. However, using a modular system such as implants 1 and 2, the surgeon may leave the stem component 10 securely implanted in the bone and simply replace the primary anatomic metaphysis M with metaphysis 20, according to embodiments of the present invention. FIGS. 45 and 46 illustrate the same stem 10 implanted into the bone B, but with the reverse metaphysis 20 and insert 30 implanted and installed after the conversion procedure, according to embodiments of the present invention. The interface 450 between the metaphysis 20 and the stem 10 is below the resection surface 51, which may be (but is not necessarily) the same resection surface 51 that was made during a primary anatomic shoulder implant. According to embodiments of the present invention, no part of the interface 450 extends outside of the bone B when modular reverse implant 1 is implanted. FIG. 46 illustrates a cross-sectional view of the metaphysis 20 secured to stem 10 with screw 40, and insert 30 locked into metaphysis 20, according to embodiments of the present invention.

One benefit of having the interface 450 below the resection surface 51 is that it permits the modular reverse prosthesis 1 to achieve a proper offset distance, compared with other reverse implants which are attached to the stem component above the resection surface and which therefore extend the center of rotation of the shoulder to a point further and further from the point providing the optimal mechanical advantage for the relevant muscles. Placing the interface 450 below the resection surface 51 thus recreates the proper kinematics for a reverse shoulder prosthesis, for example the Grammont or Grammont-style kinematics.

Figure 47:
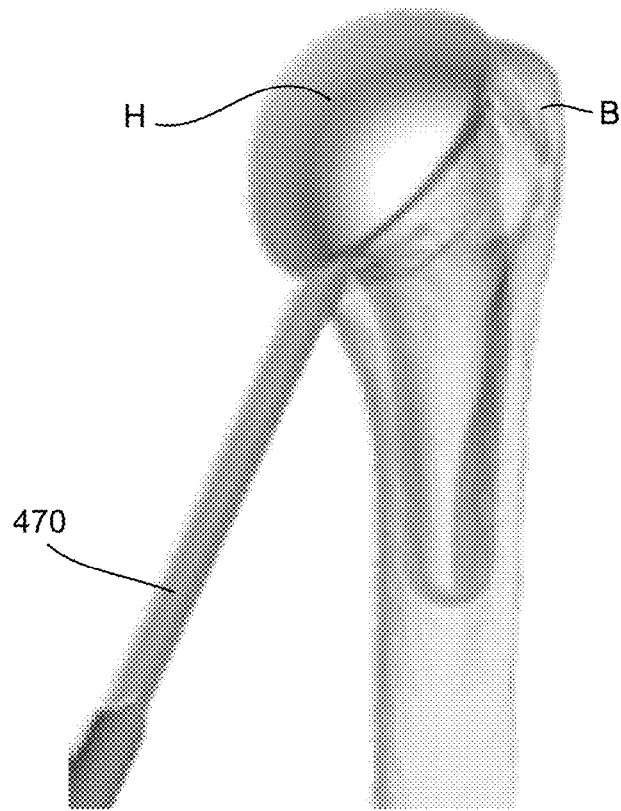
FIG. 47 illustrates removal of a modular anatomic head during an anatomic-to-reverse conversion procedure, according to embodiments of the present invention.
Figure 48:
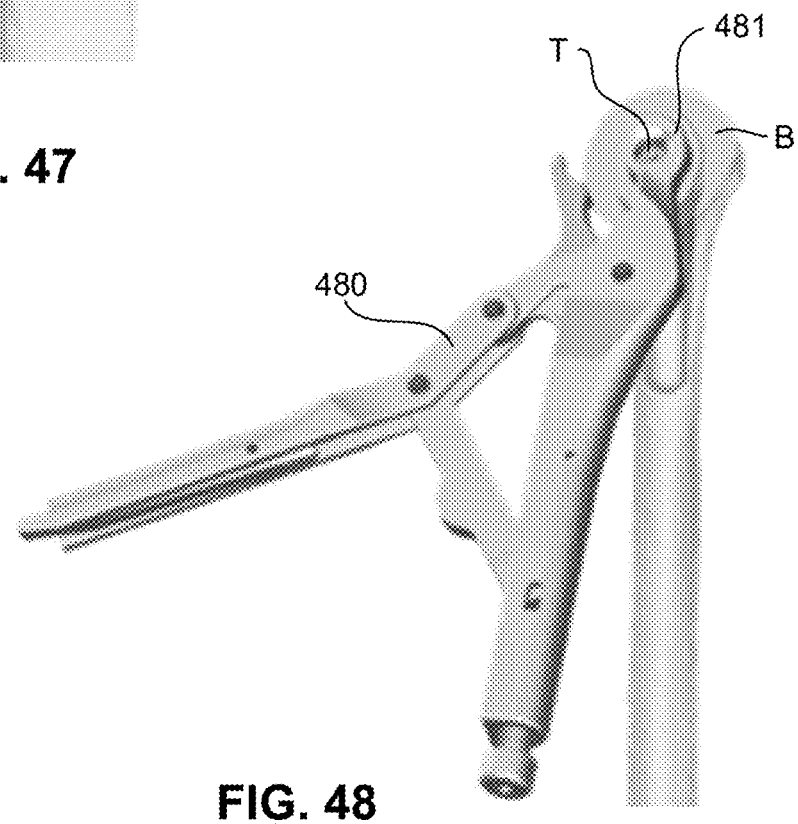
FIG. 48 illustrates attachment of an anatomic implant extractor to a proximal taper of an anatomic metaphysis during an anatomic-to-reverse conversion procedure, according to embodiments of the present invention.
Figure 49:
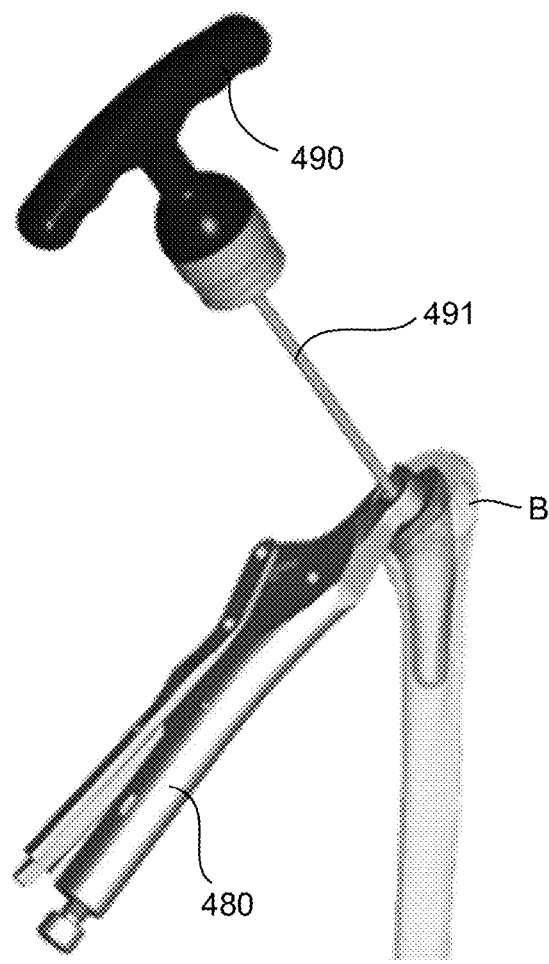
FIG. 49 illustrates insertion of a driver tool into the head of a screw holding the anatomic metaphysis to the distal stem during an anatomic-to-reverse conversion procedure, according to embodiments of the present invention.
Figure 50:
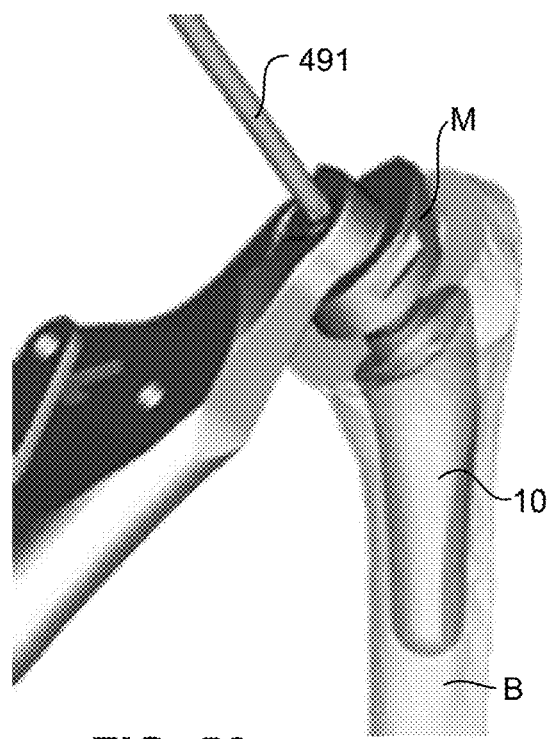
FIG. 50 illustrates loosening of the screw holding the anatomic metaphysis to the distal stem during an anatomic-to-reverse conversion procedure, according to embodiments of the present invention.

FIGS. 47 to 50 illustrate one procedure for converting a modular anatomical shoulder implant 2 into a modular reverse shoulder implant 1, according to embodiments of the present invention. As illustrated in FIG. 47, the anatomic humeral head H may be removed using an osteotome instrument 470, according to embodiments of the present invention. FIG. 48 illustrates an anatomic implant extractor 480 attached to the proximal taper T of the metaphysis M and locked into place, similar to the locking of a vice grip tool, according to embodiments of the present invention. The implant extractor 480 has a customized tip that mates with the taper T. The implant extractor 480 has a flange 481 which extends partially over the hole in the proximal taper T, while also permitting access of a driving tool into such hole. FIG. 49 illustrates the insertion of the shaft of a driver tool 491 through the hole in the proximal taper T while implant extractor 480 is attached to taper T. Turning the handle 490 in order to loosen the screw that retains the metaphysis M to the stem 10 causes the head of the screw to abut the flange 481 of the extractor 480, instead of causing the screw to exit the proximal taper T, such that continuing to loosen the screw with the driver 481 causes the entire metaphysis M to release and separate from the stem 10, as illustrated in FIG. 50. This permits the metaphysis M to be more easily removed from the stem 10 and surrounding bone B.

Figure 51:
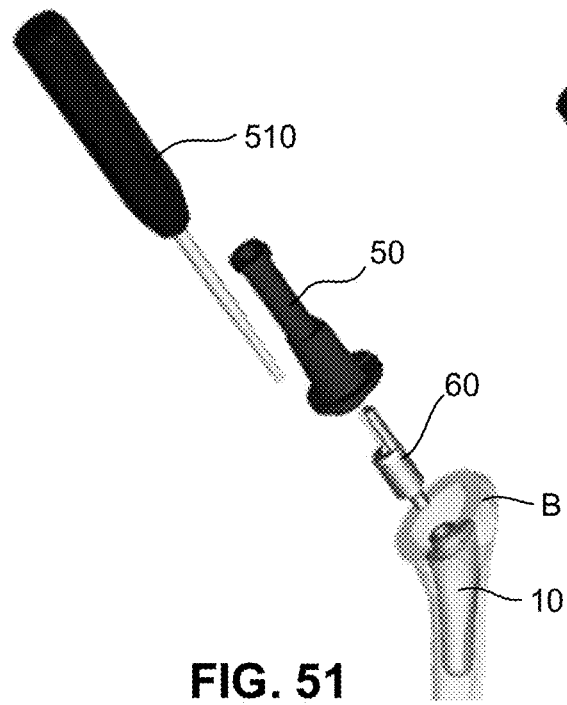
FIG. 51 illustrates insertion of a reamer guide into the taper portion of the distal stem and an offset indicator over the reamer guide in an anatomic-to-reverse conversion procedure, according to embodiments of the present invention.
Figure 52:
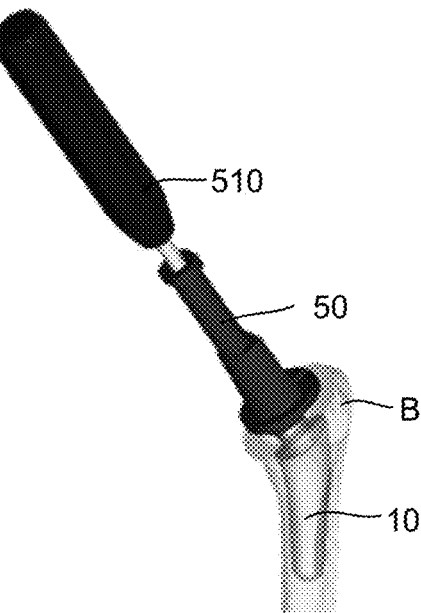
FIG. 52 illustrates insertion of a driving tool through the offset indicator and reamer guide and into contact with a reamer guide retention screw, during an anatomic-to-reverse conversion procedure, according to embodiments of the present invention.

The stem 10 may be left implanted in the bone B when converting between an anatomical implant 2 and a reverse implant 1, according to embodiments of the present invention. FIGS. 51 to 73 illustrate one procedure for implanting components of a modular reverse prosthesis 1, regardless of whether the stem 10 is implanted in a primary reverse surgery or remains implanted during a conversion from a primary anatomic to a reverse surgery. FIGS. 51 and 52 illustrate the use of offset indicator 50 and reamer guide 60 in preparing the bone B for the metaphysis 20, according to embodiments of the present invention.

FIGS. 56-61 illustrate the offset indicator 50 in greater detail, and FIGS. 62-66 illustrate the reamer guide 60 in greater detail. The offset indicator 50 includes a base 51, a reamer guide cover 53, and a neck portion 54. The base 51 includes an angle indicator 52. The neck portion 54 includes an aperture 540 for receiving a driving tool, and the reamer guide cover 53 includes an aperture 530 for receiving the reamer guide portion 63 and an aperture 531 for receiving the reamer guide portion 62, according to embodiments of the present invention. The apertures 540, 530, and 531 are in communication with one another, such that a continuous hole is formed in offset indicator 50 from the distal end 55 to the proximal end 56, according to embodiments of the present invention. The reamer guide 60 includes a proximal end 632, which is also the proximal end 632 of the reamer guide portion 63, and the reamer guide portion 62 includes a proximal surface 625, according to embodiments of the present invention.

Figure 65:
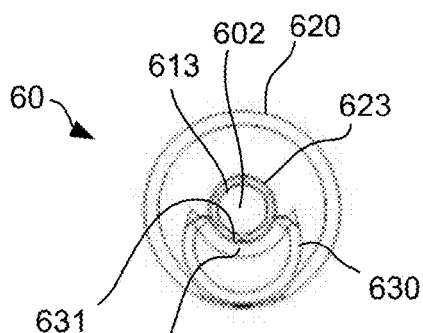
FIG. 65 illustrates a top plan view of the reamer guide of FIG. 62, according to embodiments of the present invention.
Figure 62:
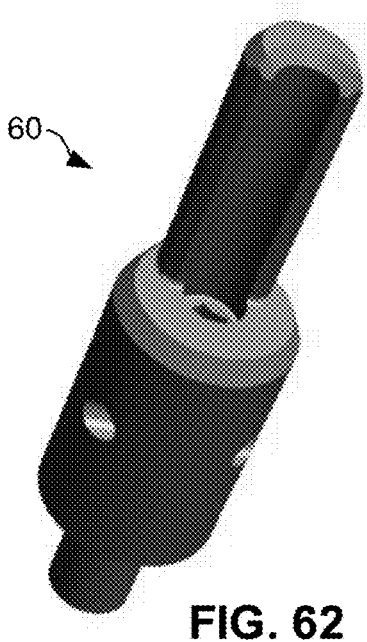
FIG. 62 illustrates a front perspective view of a reamer guide, according to embodiments of the present invention.

Reamer guide 60 includes a reamer guide portion 62 and another reamer guide portion 63 proximal to portion 62. As shown in FIG. 65, the outer surface 620 of reamer guide portion 62 is cylindrical. The outer surface 630 of the reamer guide portion 63 includes a portion of a cylinder, and may have a crescent-shaped cross section, according to embodiments of the present invention. The portion 631 of the outer surface 630 closest to hole 623 is concave in shape in order to permit access of a driving tool to hole 623, while the outer portion of outer surface 630 is convex in order to guide an inner diameter of a rotating reamer, according to embodiments of the present invention. Because the reamer guide 60 permits offset reaming, no portion of the upper reamer guide portion 63 extends radially beyond a diameter of the lower reamer guide portion 62, so as not to interfere with rotation of a reamer about the lower reamer guide portion 62, according to embodiments of the present invention. It may be desirable to provide the upper reamer guide portion 63 with a certain minimal diameter in order to provide good stability and tolerances for guiding the reamer; however, in order to use the same reamer guide 60 for both reamers, and because the reamer axis 602 for lower reamer guide portion 62 and the reamer axis 604 for upper reamer guide portion 63 are so close together, the upper reamer guide portion 63 is not cylindrical in cross section, but only partially cylindrical in cross section to permit driver access to hole 623, as shown in FIGS. 62-66, according to embodiments of the present invention. Axis 604 is the axial centerline of the cylinder of which the outer surface 630 is a portion, according to embodiments of the present invention. And axis 602 is the axial centerline of outer surface 620, according to embodiments of the present invention.

Reamer retention screw 61 extends within the reamer guide portion 62. The reamer retention screw 61 includes a radial groove 612, a stop 611, and a body portion 610, which may be all or partially threaded in order to be threadably engaged with hole 142 of stem 10, according to embodiments of the present invention. The reamer retention screw 61 may be inserted into the reamer guide portion 62 until stop 611 abuts distal end 626 of reamer guide portion 62, and secured using one or more retention mechanisms 624, 625. According to embodiments of the present invention, retention mechanisms 624, 625 interact with radial groove 612 to prevent axial movement of the screw 61 with respect to the reamer guide portions 62, 63, while permitting rotation of the screw 61 with respect to the reamer guide portions 62, 63 so that the screw 61 may be threadably tightened into hole 142 of stem 10. Holes 621, 622 may be provided in reamer guide portion 62 in order to permit installation of retention mechanisms 624, 625, which may be adhesive and/or one or more set screws and/or rods, according to embodiments of the present invention. Screw 61 also includes an aperture 613 configured to interface with a driver tool 510, according to embodiments of the present invention. Driver tool 491 may be the same as or similar to driver tool 510, according to embodiments of the present invention.

Figure 67:
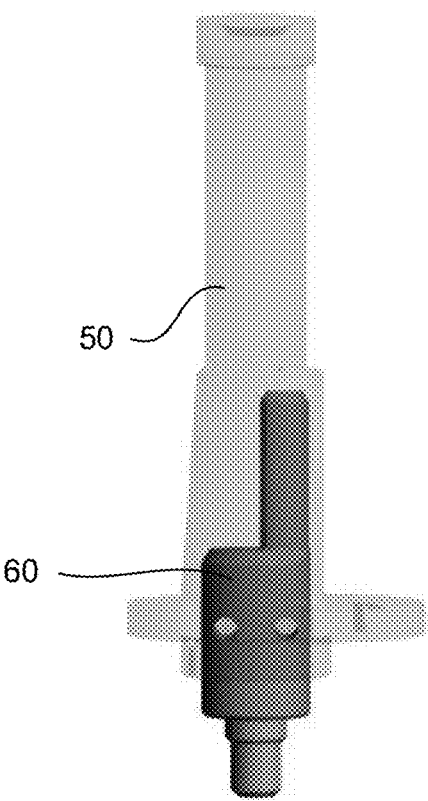
FIG. 67 illustrates a side view of an offset indicator superimposed over a reamer guide, according to embodiments of the present invention.

The inner shape of at least a portion of openings 530 and 531 conforms to an outer shape of at least a portion of the reamer guide portions 62 and 63, such that when the offset indicator 50 is inserted over reamer guide 60 (as illustrated in FIG. 67), the axial centerline axis 541 of apertures 540 and 531 is aligned with the axis 602 of reamer guide 60, and the reamer guide 60 rotates as one with the offset indicator 50 about axis 602, according to embodiments of the present invention. An o-ring 515 or the like (see FIG. 58) may help releasably retain the reamer guide 60 inside of the offset indicator 50, according to embodiments of the present invention. In other words, when the offset indicator 50 is engaged with reamer guide 60 as shown in FIG. 67, the reamer guide 60 has no, or negligible, freedom of rotation with respect to offset indicator 50. However, the entire offset indicator 50 and reamer guide 60 assembly rotates about the screw 61 about axis 602, until the screw is tightened.

The angle indicator 52 of offset indicator 50 indicates a certain angular orientation with respect to the eccentricity of the axis 602 as it relates to the axis 604, which corresponds to the offset eccentricity between axes 29 and 290 of reverse metaphysis 20, according to embodiments of the present invention. In the example shown in FIGS. 56-61, the angle indicator 52 is located in a radial position corresponding to a maximum offset distance. This radial position is an extension (substantially in the plane of the view of FIG. 65) of the line connecting the axis 602 with the axis 604, and is formed at a location along such line that is closer to the axis 604 than 602, according to embodiments of the present invention. In this way, the surgeon may begin threading the screw 61 into the hole 142, but before tightening the screw 61, rotate the assembly of the offset indicator 50 and reamer guide 60 about axis 602 until a desired angular orientation is achieved. The surgeon may select the desired angular orientation with respect to the eccentricity of the metaphysis 20 in order to achieve the best fit of the metaphysis 20 with the surrounding bone B, according to embodiments of the present invention. Once the desired angle is found, the surgeon may use angle indicator 52 to make a mark in or on the bone B corresponding to the position of the angle indicator 52. This mark may be made outside of the eventual reaming boundary, so that it is still visible after reaming, according to embodiments of the present invention.

In addition to or instead of the angle indicator 52 indicating the maximum eccentricity, the outer surface 510 of the base 51 of the offset indicator 50 may be shaped to correspond, roughly or exactly, to the outer perimeter shape of the metaphysis 20, such that when the offset indicator 50 is rotated about axis 602, the surgeon visually sees the "footprint" of the metaphysis 20 as the offset eccentricity rotates. Once the surgeon has selected the desired angular orientation for the metaphysis 20 using the offset indicator 50, the surgeon tightens screw 61 into the hole 142, thereby locking the angular orientation of the reamer guide 60 with respect to the stem 10. At this stage, the reamer guide 60 is ready to guide the reaming process.

Figure 53:
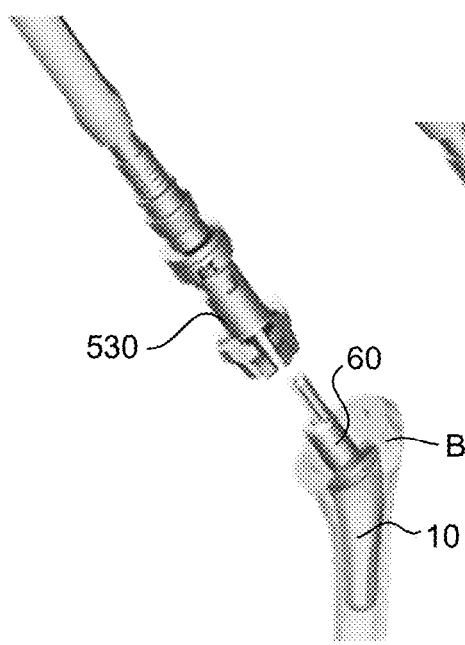
FIG. 53 illustrates a body reamer going over the reamer guide during an anatomic-to-reverse conversion procedure, according to embodiments of the present invention.
Figure 54:
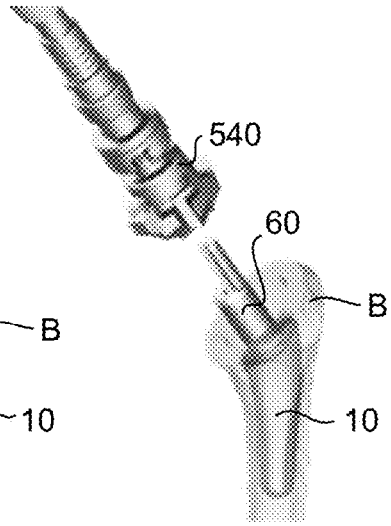
FIG. 54 illustrates a rim reamer going over the reamer guide during an anatomic-to-reverse conversion procedure, according to embodiments of the present invention.
Figure 68:
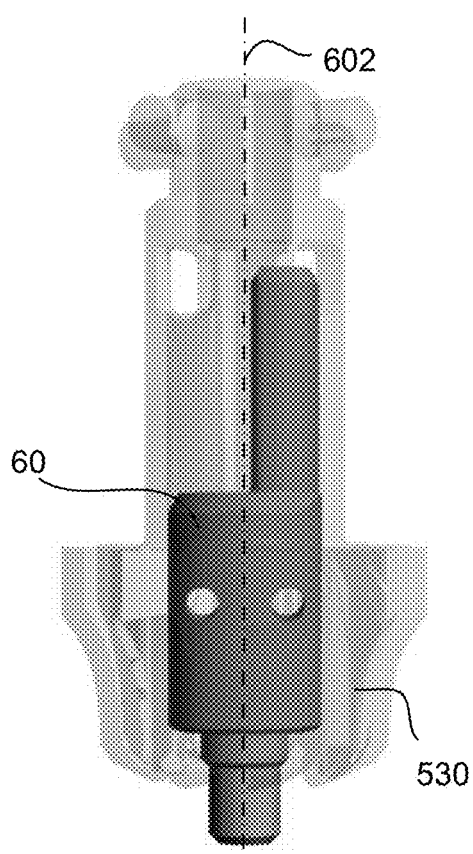
FIG. 68 illustrates a side view of a body reamer superimposed over a reamer guide, according to embodiments of the present invention.
Figure 69:
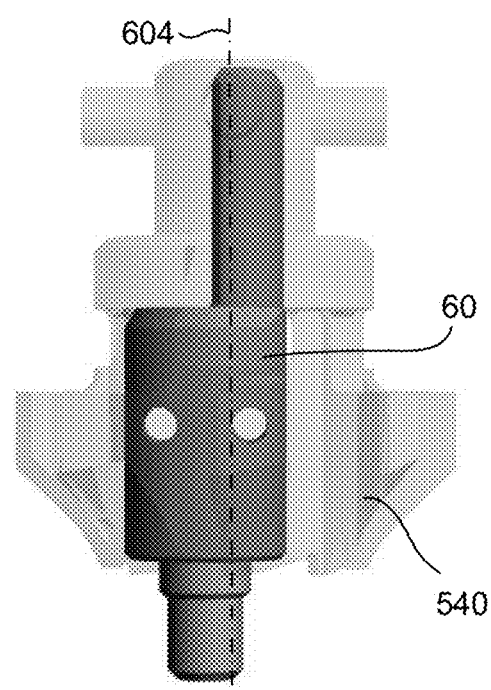
FIG. 69 illustrates a side view of a rim reamer superimposed over a reamer guide, according to embodiments of the present invention.
Figure 70:
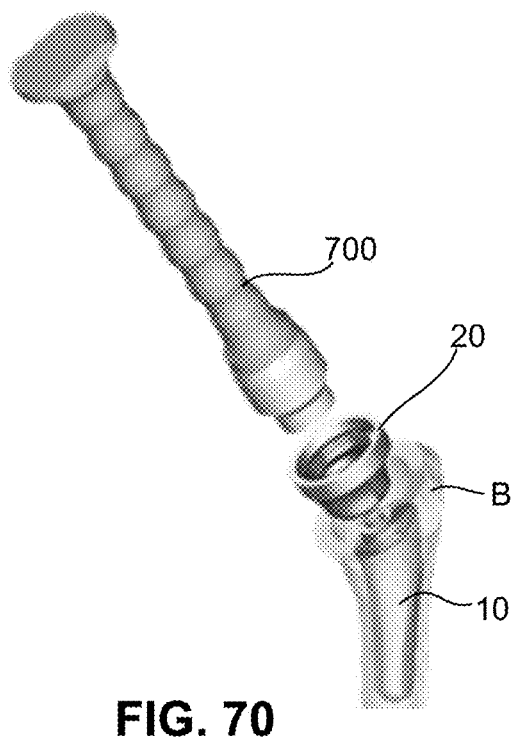
FIG. 70 illustrates an impactor used to impact a reverse metaphysis onto the distal stem during an anatomic-to-reverse conversion procedure, according to embodiments of the present invention.

FIG. 53 illustrates a body reamer 530 inserted over the reamer guide 60, according to embodiments of the present invention. As illustrated in FIG. 68, an inner diameter of the body reamer 530 is inserted over and interfaces with the outer diameter 620 of the distal reamer guide portion 62 to guide the reaming (about axis 602) of the "body" portion of the bone B which will accept the distal end of the metaphysis 20, according to embodiments of the present invention. FIG. 54 illustrates a rim reamer 540 inserted over the reamer guide 60, according to embodiments of the present invention. As illustrated in FIG. 69, an inner diameter of the rim reamer 540 is inserted over and interfaces with the outer diameter 630 of the proximal reamer guide portion 63 to guide the reaming (about axis 604) of the "rim" portion of the bone B which will accept the proximal end of the metaphysis 20, according to embodiments of the present invention. These two different types of reaming may be done in any order, and may be accomplished using the same dual-axis reamer guide 60, according to embodiments of the present invention. Also, alternatively, the inner diameter of the body reamer 530 may be configured to be guided by the proximal reamer guide portion 63 and the inner diameter of the rim reamer 540 may be configured to be guided by the distal reamer guide portion 62, according to embodiments of the present invention. A reamer which uses the proximal reamer guide portion 63 for guidance also has a larger diameter clearance distally of the inner diameter of the reamer part that interfaces with surface 630, so as not to interfere with surface 620, according to embodiments of the present invention.

According to embodiments of the present invention, the reamers 530 and/or 540 may be configured to employ proximal surfaces 625 or 632 of reamer guide 60 as stops, to stop the distal advancement of the reamers 530 and/or 540 at a proper depth with respect to the stem 10 and/or resection surface 51. The reamers 530 and/or 540 may also include one or more windows, and the reamer guide 60 may also include depth markings visible through the one or more windows even during reamer rotation in order to guide the surgeon in reaming to the proper depth, according to embodiments of the present invention.

Figure 55:
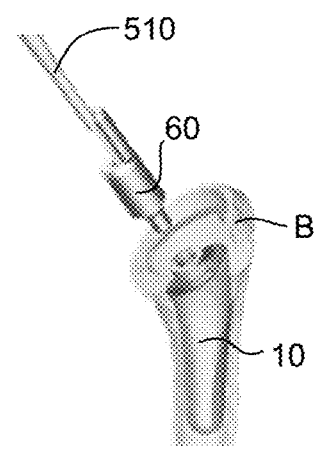
FIG. 55 illustrates removal of the reamer guide from the distal stem during an anatomic-to-reverse conversion procedure, according to embodiments of the present invention.
Figure 56:
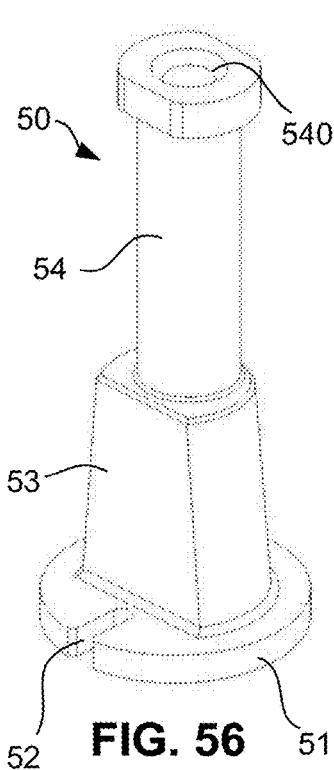
FIG. 56 illustrates a front perspective view of an offset indicator, according to embodiments of the present invention.
Figure 58:
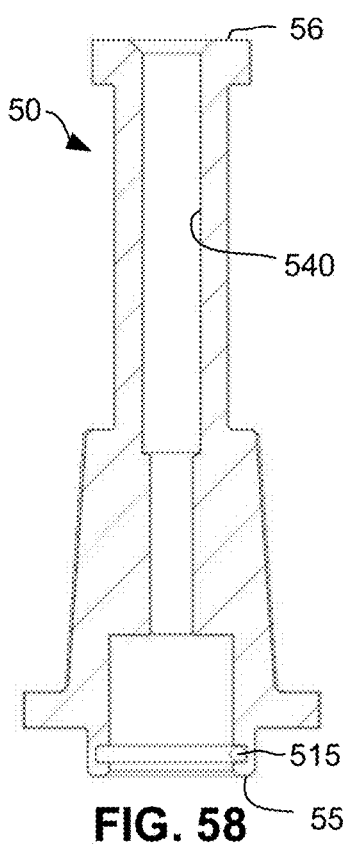
FIG. 58 illustrates a back cross-sectional view of the offset indicator of FIG. 57, according to embodiments of the present invention.
Figure 60:
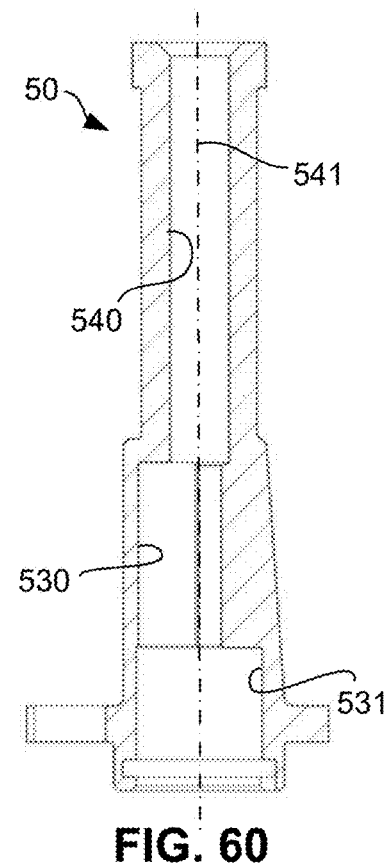
FIG. 60 illustrates a side cross-sectional view of the offset indicator of FIG. 59, according to embodiments of the present invention.
Figure 61:
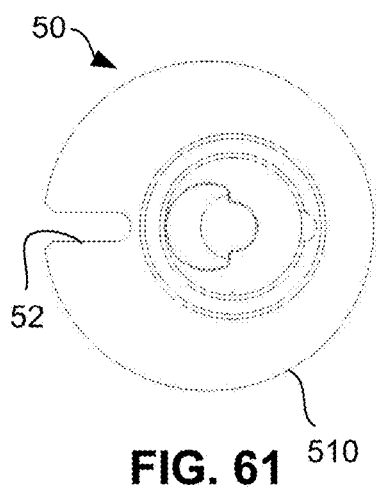
FIG. 61 illustrates a bottom plan view of the offset indicator of FIG. 56, according to embodiments of the present invention.
Figure 57:
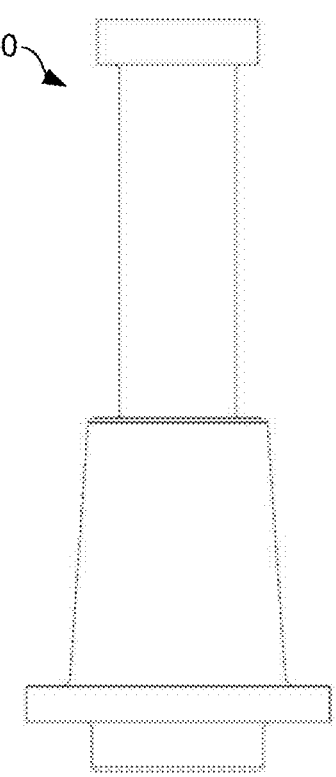
FIG. 57 illustrates a back elevation view of the offset indicator of FIG. 56, according to embodiments of the present invention.
Figure 59:
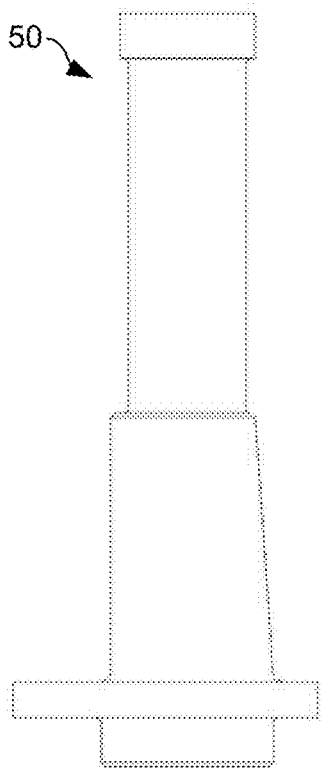
FIG. 59 illustrates a side elevation view of the offset indicator of FIG. 56, according to embodiments of the present invention.
Figure 63:
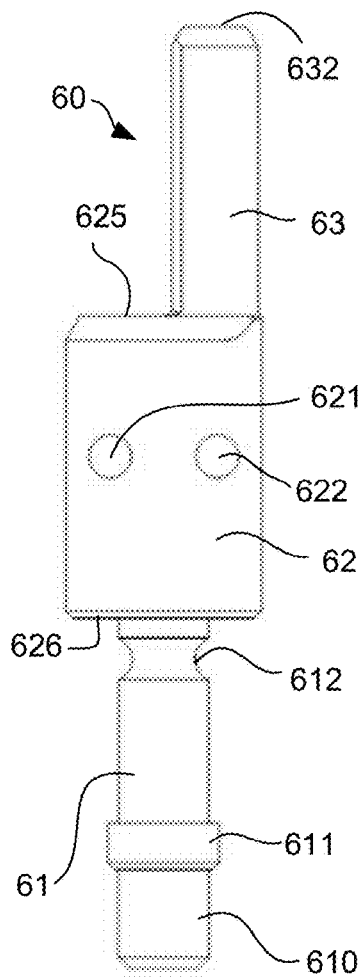
FIG. 63 illustrates a side perspective view of a reamer guide with a reamer guide retention pin unsecured, according to embodiments of the present invention.
Figure 64:
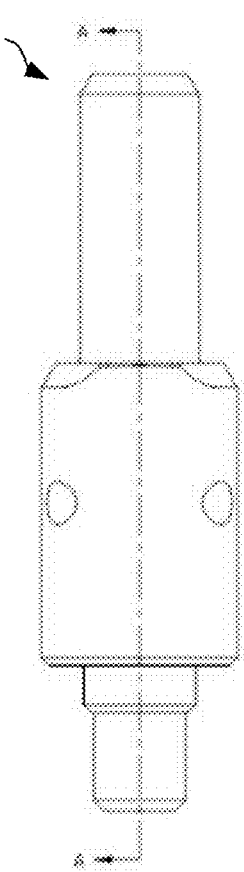
FIG. 64 illustrates a back perspective view of the reamer guide of FIG. 62, according to embodiments of the present invention.
Figure 66:
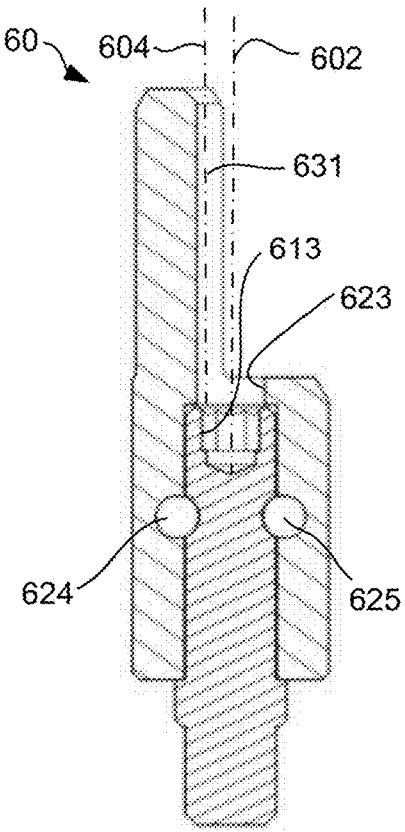
FIG. 66 illustrates a side cross-sectional view of the reamer guide of FIG. 64, taken along line A-A of FIG. 64, according to embodiments of the present invention.

As illustrated in FIG. 55, once the reaming has been performed, the screw 61 may be loosened, and the reamer guide 60 removed from the stem 10. The reverse metaphysis 20 may then be inserted into the distal stem 10, aligning the metaphysis 20 with the mark previously made with angle indicator 52. For example, the reference number and marking corresponding to "1" on the side of the metaphysis 20 (see FIG. 18) may correspond to the maximum eccentricity of metaphysis 20 in the same way that the angle indicator 52 corresponds to the maximum eccentricity; in such cases, the number "1" on the metaphysis 20 may be aligned with the mark made from angle indicator 52 prior to impacting the insert 30 into place with an impactor 700 to ensure proper alignment, according to embodiments of the present invention. In addition to or instead of the markings 200, one or more of the fins 28 may be used in the same way as an index position for aligning with the mark made from the angle indicator 52, according to embodiments of the present invention. During impaction of the metaphysis 20 onto the stem 10, the fins 28 of the metaphysis 20 embed themselves in the surrounding bone B, thereby further strengthening the fit of the metaphysis 20 with the surrounding bone B and further deterring movement and/or rotation of the metaphysis 20 once implanted.

Figure 71:
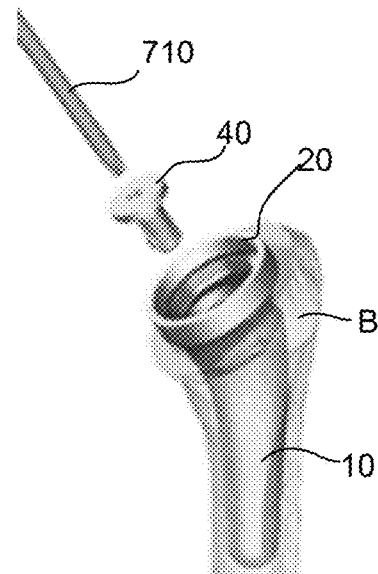
FIG. 71 illustrates insertion of a modular screw to attach the reverse metaphysis onto the distal stem during an anatomic-to-reverse conversion procedure, according to embodiments of the present invention.
Figure 72:
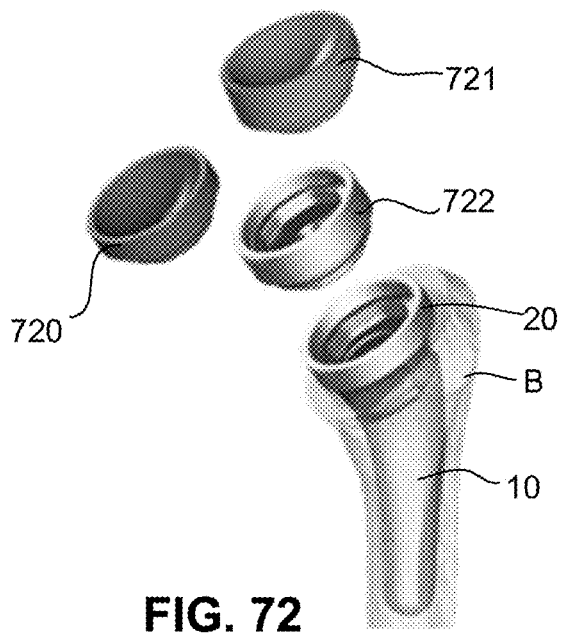
FIG. 72 illustrates various trial inserts being tried during an anatomic-to-reverse conversion procedure, according to embodiments of the present invention.
Figure 73:
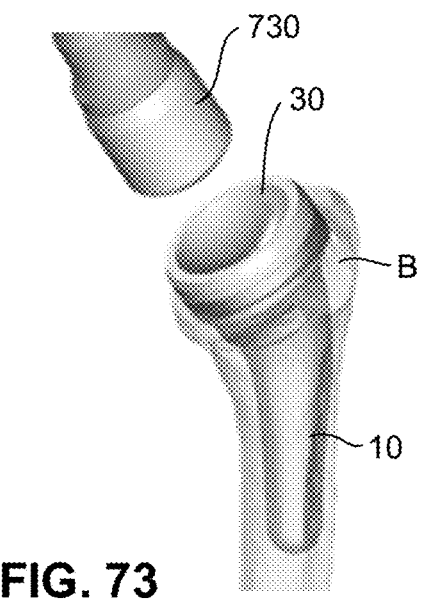
FIG. 73 illustrates impaction of the selected reverse insert into the reverse metaphysis during an anatomic-to-reverse conversion procedure, according to embodiments of the present invention.
Figure 74:
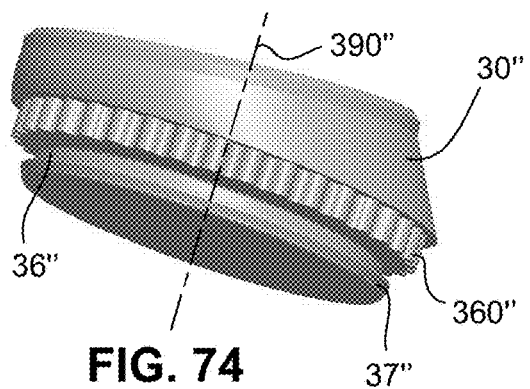
FIG. 74 illustrates a front perspective view of an alternative reverse insert, according to embodiments of the present invention.

Once the metaphysis 20 is in place, the modular assembly screw 40 may be inserted through holes 26, 230, and 23 (see FIG. 16) and into hole 142 of stem 10 (see FIG. 10), and tightened, as illustrated in FIG. 71. Optional insert trialing may then be performed using trial inserts 720, 721, and/or extenders 722, as illustrated in FIG. 72. Once the insert 30, as well as its orientation, has been selected for implant, the insert 30 is impacted into place using an impactor 730, according to embodiments of the present invention. As described above, the visual markings 200 on the metaphysis 20 include eight position markers and the numbers one through eight, one at each equally spaced marker, to indicate the location at which the indexing marker 300' of an angled insert 30' should align such that the octagonal locking protrusion 36' is aligned with the octagonal opening 25 of the metaphysis 20. A similar marker may be included on one or more trial inserts 720, 721, so that the surgeon can replicate the angular position of the trial with the angular position of the insert 30 using the markers, according to embodiments of the present invention.

A modular reverse shoulder prosthesis 1 according to embodiments of the present invention has an aesthetically pleasing and sleek looking radiographic profile in x-ray images. Because of the concavity 13 on the proximal end of the stem 10 (see FIGS. 5-10) between the base 140 of the proximal taper 14 and the proximal perimeter 12 of the stem 10, the base 140 is not visible in either of the side views of FIG. 6 or 7 (which may correspond, for example, to the views taken in the coronal plane), according to embodiments of the present invention. The curved portion of the concavity 13 may extend in all directions outwardly from the base 140, according to embodiments of the present invention. As such, because the convex curved portion 27 of the distal end 21 of the metaphysis 20 interfaces with the concave portion 13 of the stem 10 when the metaphysis 20 is attached to the stem 10, the distal end 21 of the metaphysis 20 is also not visible in either side view (e.g. the side views corresponding to FIG. 6 or 7) because it is hidden by the skirt created by the proximal perimeter 12 and concavity 13. The skirt 12 hides the modular connection gap between the stem 10 and metaphysis 20. This creates a very sleek radiographic profile in which the metaphysis 20 and stem 10 appear to be one single component, and/or in which the gaps visible between the metaphysis 20 and the stem 10 are minimized. The same is true of the metaphysis M and stem 10 of the anatomic prosthesis 2, according to embodiments of the present invention. FIGS. 36, 37, 38, 40, 42, and 44-46 also illustrate this characteristic of prostheses 1, 2. According to embodiments of the present invention, the distalmost end 21 of metaphysis 20 is covered by the proximal perimeter 12 for the side views (e.g. views taken in the coronal plane) of the implant 1 for any rotational orientation, or an unlimited number of rotational orientations, of the metaphysis 20 with respect to the stem 10.

As used herein, the terms coronal plane, sagittal plane, and transverse (axial) plane are used in their ordinary sense to refer to the anatomical planes of the human body, and when used with respect to implant 1, are used to refer to the implant when the arm is in the lowered position with the fingers pointing downward and with the primary coronal, sagittal, and transverse planes intersecting at the implant 1.

Embodiments of the present invention include an infinitely dialable eccentric reverse metaphysis 20 component, which allows for a best fit of the patient's proximal humerus. A unique short stem design with a taper angled at 145 degrees allows the dialability to occur about the axis 29 of the metaphysis 20 (which also corresponds to axis 143), rather than being limited to dialability about the primary stem 10 axis, or the primary longitudinal axis of the stem 10, according to embodiments of the present invention. The instrumentation used to implant prostheses 1, 2 includes instrumentation for eccentric reaming, broaching, and trialing, according to embodiments of the present invention.

A metaphysis 20 according to embodiments of the present invention provides infinite eccentric dialability along the axis of the metaphysis 20 (perpendicular to the resection plane, at a 145° resection angle) to provide the best fit to the patient's proximal humerus, allowing for optimal press fit fixation, according to embodiments of the present invention. Also, the reverse inserts 30, 30' mate with the reverse metaphysis 20 via an octagonal locking mechanism; the inserts 30 contain a thin barb feature 37 that wraps around an octagonal protrusion 36. The reverse metaphysis 20 has a mating octagonal hole 25 with octagonal threads 250 machined into it. The inserts 30 are impacted in and the barb feature 37 engages with the octagonal threads 250, thus permitting angled or straight inserts to be positioned in eight different orientations, according to embodiments of the present invention.

Figure 75:
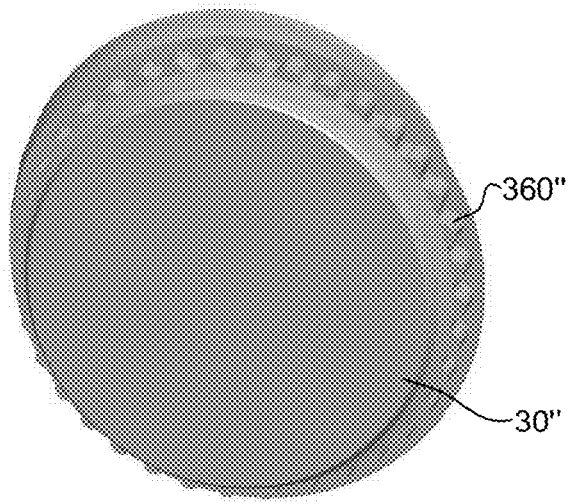
FIG. 75 illustrates a bottom perspective view of the alternative reverse insert of FIG. 74, according to embodiments of the present invention.
Figure 76:
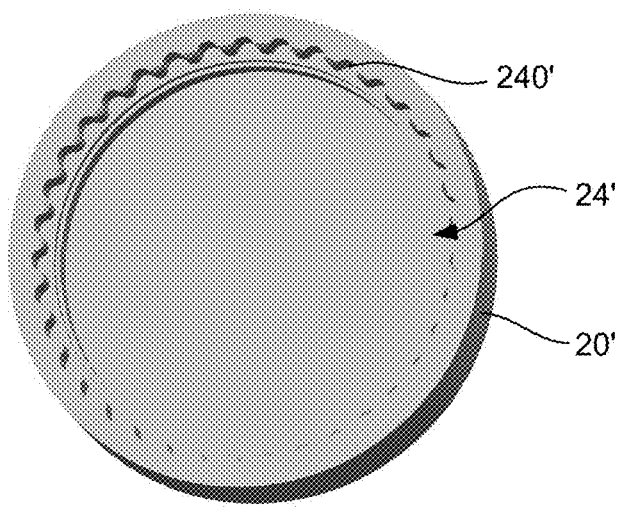
FIG. 76 illustrates a top perspective view of an alternative reverse metaphysis configured to mate with the alternative reverse insert of FIGS. 74 and 75, according to embodiments of the present invention.
Figure 77:
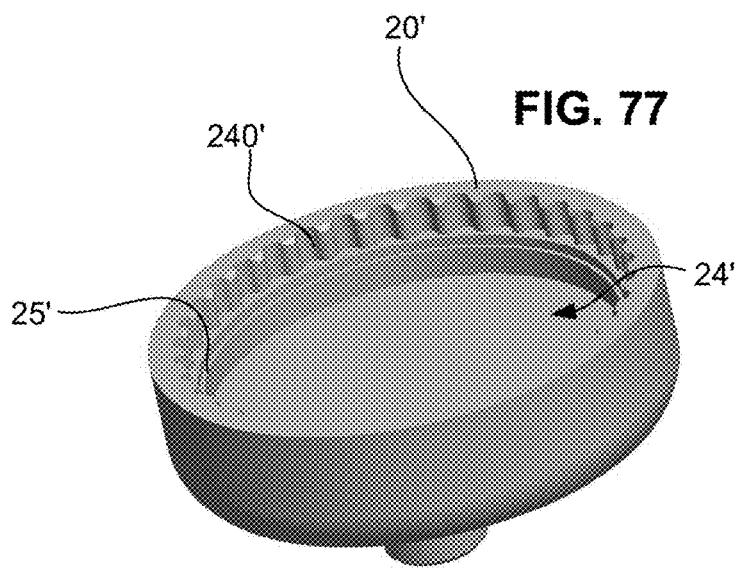
FIG. 77 illustrates a front perspective view of the alternative reverse metaphysis of FIG. 76, according to embodiments of the present invention.
Figure 78:
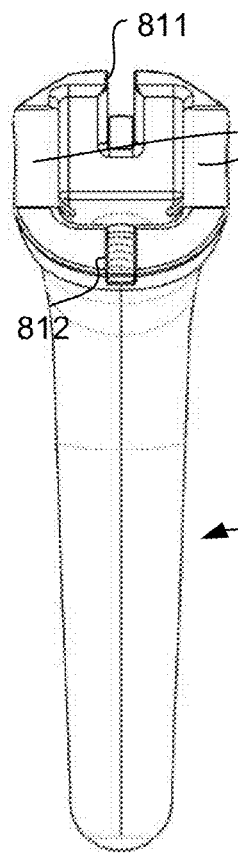
FIG. 78 illustrates a front elevation view of a distal stem portion of an adjustable angle shoulder prosthesis stem, according to embodiments of the present invention.
Figure 79:
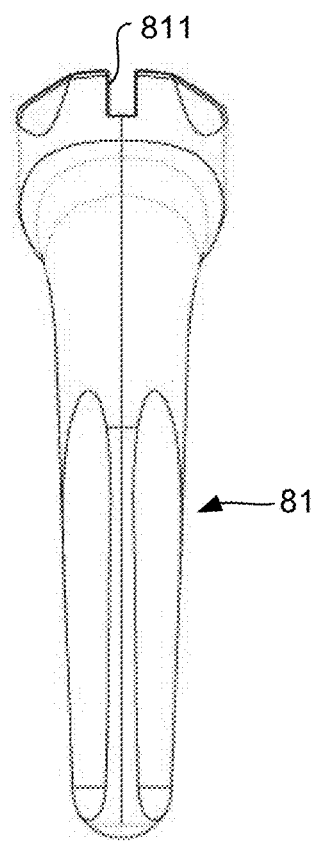
FIG. 79 illustrates a rear elevation view of the distal stem portion of FIG. 78, according to embodiments of the present invention.
Figure 80:
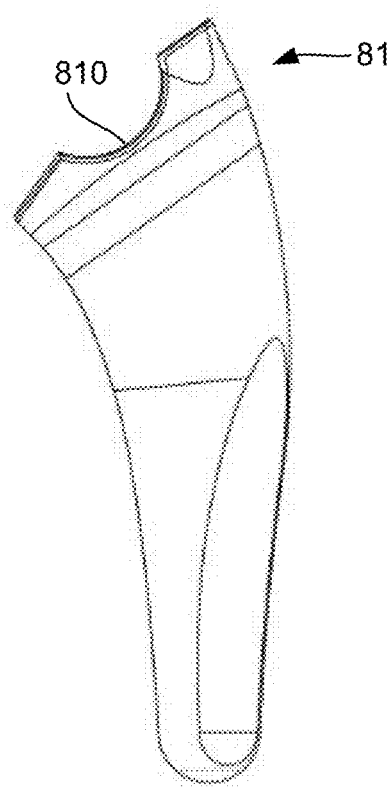
FIG. 80 illustrates a side elevation view of the distal stem portion of FIGS. 78 and 79, according to embodiments of the present invention.
Figure 81:
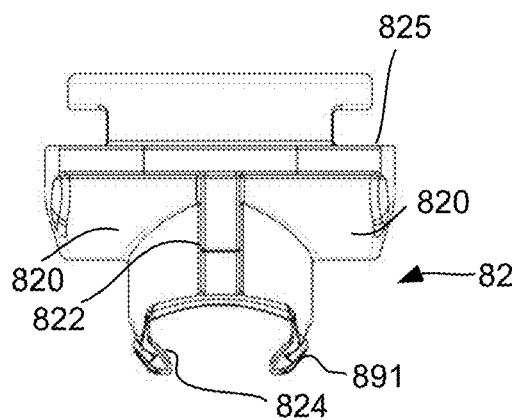
FIG. 81 illustrates a front elevation view of a proximal stem portion of an adjustable angle shoulder prosthesis stem, according to embodiments of the present invention.
Figure 82:
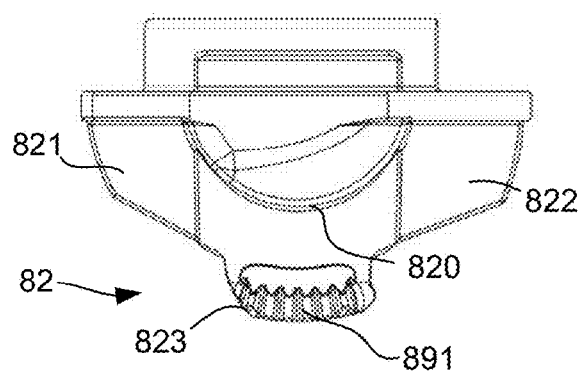
FIG. 82 illustrates a side elevation view of the proximal stem portion of FIG. 81, according to embodiments of the present invention.
Figure 83:
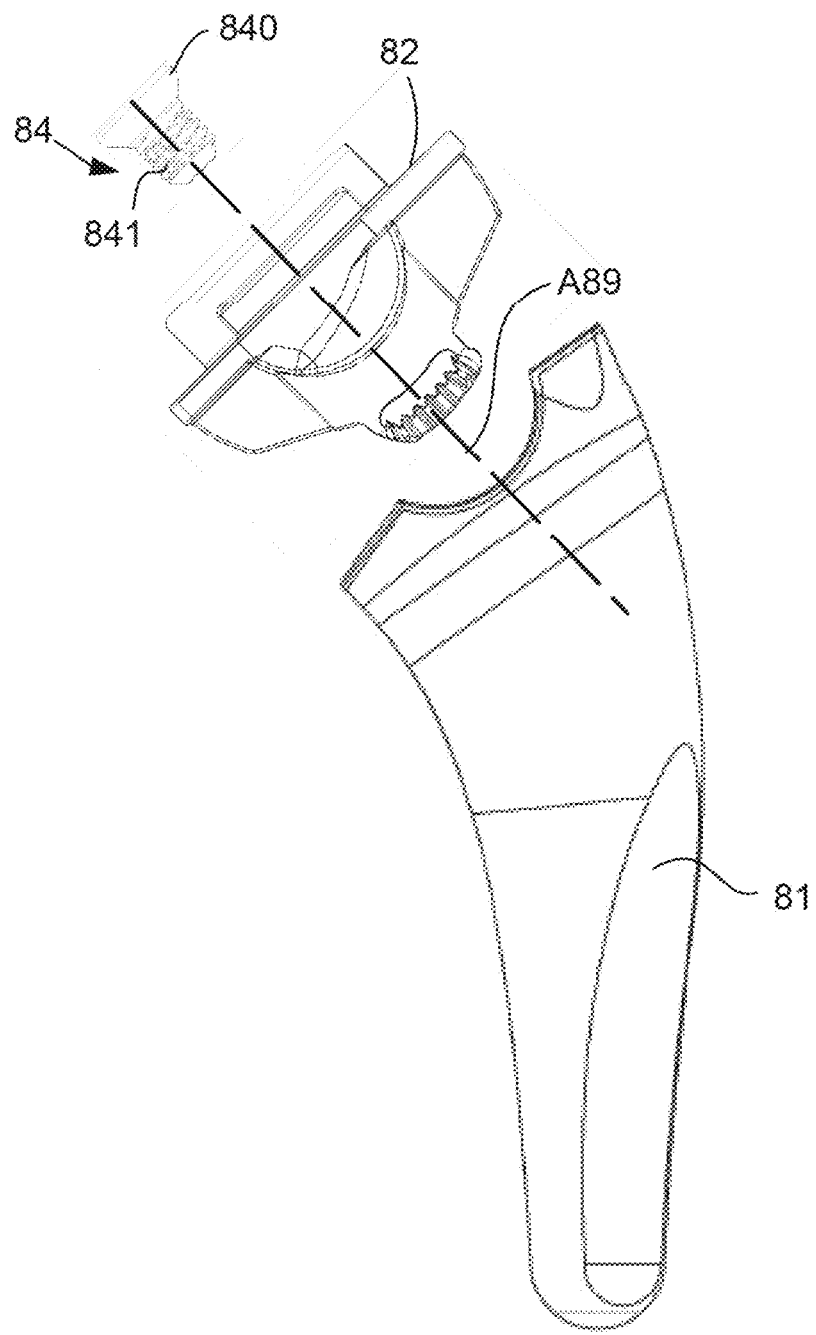
FIG. 83 illustrates an exploded side elevation view of an adjustable angle shoulder prosthesis stem, according to embodiments of the present invention.

FIGS. 75 to 77 illustrate an alternative reverse metaphysis 20' and an alternative reverse insert 30", according to embodiments of the present invention. Insert 30" includes a distal protrusion 36" which is configured for interlocking interface with an aperture 24' in reverse metaphysis 20', according to embodiments of the present invention. An outer surface of the distal protrusion 36" includes teeth 360" which are configured to mate with and interlock with complementary teeth 240' in the aperture 24', according to embodiments of the present invention. Distal protrusion 36" also includes a locking lip 37" similar to locking lips 37 and 37'; locking lip 37" is configured to engage with a rim 25' in aperture 24' when insert 30" is inserted into metaphysis 20', according to embodiments of the present invention. The teeth 360" and 240' may be rotationally symmetrical about an axis 390" when insert 30" is interlocked with metaphysis 20', according to embodiments of the present invention. According to embodiments of the present invention, the insert 30" and metaphysis 20' have an interlocking rotational symmetry of an order of five to thirty-six; for example, the insert 30" and metaphysis 20' shown in FIGS. 74 to 77 include an interlocking rotational symmetry of an order of thirty-six. According to some embodiments of the present invention, the insert 30" and metaphysis 20' (and/or the insert 30' or 30 and metaphysis 20) have an interlocking rotational symmetry of an order of two to thirty-six. In some cases, increasing the order of the interlocking rotational symmetry permits greater precision in selecting the ultimate orientation of the cup axis 380', 380" for an eccentric insert 30', depending also on the dialability of the metaphysis 20 with respect to the stem 10, according to embodiments of the present invention.

According to some embodiments of the present invention, the metaphyseal plane 203 (see FIG. 45) of the implanted modular reverse metaphysis 20 is more horizontal (e.g. at an inclination angle between 140° and 160°, for example about 145°, as measured between the normal 2030 to the metaphyseal plane 203 and the stem axis 110) than the anatomic inclination plane 202 (see FIG. 44) of the primary metaphysis M (e.g. at an inclination angle range of 125° to 145°, as measured between the normal A to the anatomical inclination plane 202 and the stem axis 110). In other words, the angle AP between the stem axis 110 and the anatomic inclination plane 202 of the primary metaphysis M is smaller than the angle AR between the stem axis 110 and the modularity plane 203 of the reverse metaphysis 20, according to embodiments of the present invention. Stated differently, for a given modularity plane MP for a given distal stem 10, in the reverse implantation, the metaphyseal plane 203 is substantially perpendicular to the modularity plane MP (e.g. the taper axis 143 which is normal to the modularity plane MP is substantially parallel to the normal 2030 to the metaphyseal plane 203), and in the primary anatomical implantation, the anatomical inclination plane 202 is more vertically oriented than the modularity plane MP (e.g. the angle between the taper axis 143 and the stem axis 110 is larger than the angle between the normal A to the anatomic inclination plane 202 and the stem axis 110). Existing anatomic-to-reverse conversions typically involve the opposite: the inclination angle for the metaphyseal plane of the reverse component is smaller than that of the anatomic inclination plane. Embodiments of the present invention permit inverse angle evolution, permitting essentially a transition from a typically reversed inclination to a typically anatomic inclination using the modular reverse inserts and reverse metaphysis.

A kit according to some embodiments of the present invention includes two or more stems 10 having different fixed anatomical angles, for example having different angles 111 formed between the stem axis 110 and the taper axis 143 (see FIG. 10), as well as a metaphysis 20 which interfaces with the two or more different stems 10 as described above, and two or more reverse inserts 30' with different cup angles. Typical reverse shoulder conversion adapters often include multiple metaphyseal elements each with different angles, and a single straight insert element; however, as the metaphyseal elements are typically metal, this existing arrangement typically increases the number of items in a kit and/or leads to increased manufacturing cost, according to embodiments of the present invention. The two or more reverse inserts 30' with different cup angles may be selected so as to correspond with the angles of the two or more stems 10 of the kit, thus permitting the resulting angle to be the same among various stem 10 and insert 30' combinations, according to embodiments of the present invention.

As illustrated in FIGS. 44 and 45, a kit according to some embodiments of the present invention includes a stem 10; a reverse metaphysis 20 which, when attached to the stem 10, results in an (obtuse) inclination angle between the normal 2030 to the metaphyseal plane 203 and the normal 143 to the modular plane MP which is substantially the same; and one or more anatomic metaphyses M which, when attached to the stem 10, each result in an (obtuse) inclination angle between the normal axis A to the anatomic inclination plane 202 and the primary stem axis 110 which is less than the (obtuse) inclination angle between the normal 143 to the modularity plane MP and the primary stem axis 110. The obtuse inclination angle between the normal 2030 and the primary stem axis 110 may be from 145° to 155°, according to embodiments of the present invention. The obtuse inclination angle between the normal axis A to the anatomic inclination plane 202 and the primary stem axis 110 may be from 125° to 140°, according to embodiments of the present invention. For example, such a kit may include two or more anatomic metaphyses M, wherein the obtuse inclination angle between the normal axis A to the plane 202 and the stem axis 110 is different for each of the two or more metaphyses M. For example, such a kit may include three anatomic metaphyses M for which such angles are 127.5°, 132.5°, and 137.5°, respectively, according to embodiments of the present invention. The distal end of the anatomic metaphysis M may be similar to the distal end of reverse metaphysis 20 for interface and attachment with the proximal taper, according to embodiments of the present invention.

Embodiments of the present invention may include one or a combination of components made partially or completely of pyrocarbon, including but not limited to stem 10, reverse metaphysis 20, anatomic metaphysis M, insert 30, and head H.

FIGS. 78-88 illustrate a shoulder prosthesis stem 80, according to embodiments of the present invention. Shoulder prosthesis stem 80 includes a distal stem portion 81 and a proximal stem portion 82. The proximal stem portion 82 includes a proximal female stem taper 813, and the proximal stem portion 82 pivots with respect to the distal stem portion 81 and is configured for attachment to the distal stem portion 81 at a range of angles with respect to the distal stem portion 81, according to embodiments of the present invention. The proximal stem portion 82 includes a proximal curved bearing surface 820, a medial fin 822, a lateral fin 821, and a proximal bearing surface 825, according to embodiments of the present invention. The distal side of the proximal stem portion 82 includes a protrusion 823 which includes a slider slot 824, according to embodiments of the present invention. The slot 824 is configured to permit a screw 84 to be accepted therethrough for connecting to a screw hole 814 in the distal stem portion 81, according to embodiments of the present invention. The screw 84 includes a head portion 840 and a shaft portion 841; the shaft portion 841 fits through the slot 824 while the slot 824 is too narrow to permit passage of the head portion 840, according to embodiments of the present invention.

Figure 88:
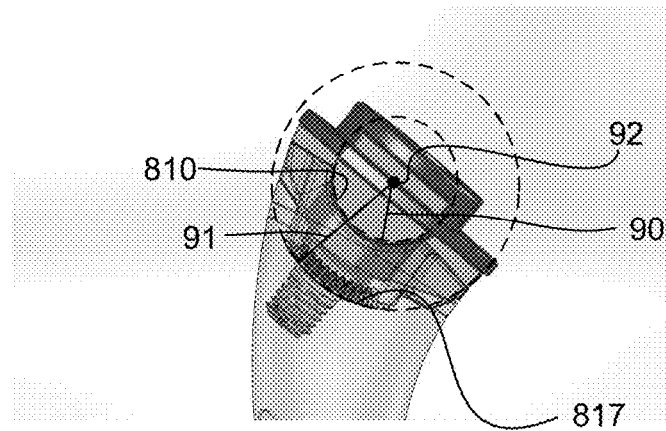
FIG. 88 illustrates the side elevation view of the adjustable angle shoulder prosthesis stem of FIG. 87, with circles superimposed thereon to illustrate the radii of curvature, according to embodiments of the present invention.

The distal stem portion 81 includes a proximal curved bearing surface 810 configured to engage with the distal curved bearing surface 820 of the proximal stem portion 82, according to embodiments of the present invention. The distal stem portion 81 also includes a lateral notch or groove 811 configured to accept the lateral fin 821, and a medial notch or groove 812 configured to accept the medial fin 822 when the proximal stem portion 82 is engaged with and/or attached to the distal stem portion 81, according to embodiments of the present invention. The proximal curved bearing surface 810 slides against the distal curved bearing surface 820 as the proximal stem portion 82 pivots with respect to the distal stem portion 81, according to embodiments of the present invention. This pivoting occurs about pivot axis 92 (see FIG. 88), which extends in a substantially medio-lateral direction (perpendicularly to the view shown in FIG. 88), according to embodiments of the present invention. As such, the proximal curved bearing surface 810 and the distal curved bearing surface 820 may be at least partially complementary; for example, both surfaces may have at least a portion formed along a radius of curvature 90 formed about the pivot axis 92, as shown in FIG. 88, according to embodiments of the present invention. The distal end 823 of the proximal stem portion 82, as well as the proximal inner surface 817, may be at least partially formed about a larger radius of curvature 91 also formed about the pivot axis 92, as shown in FIG. 88, according to embodiments of the present invention.

Figure 84:
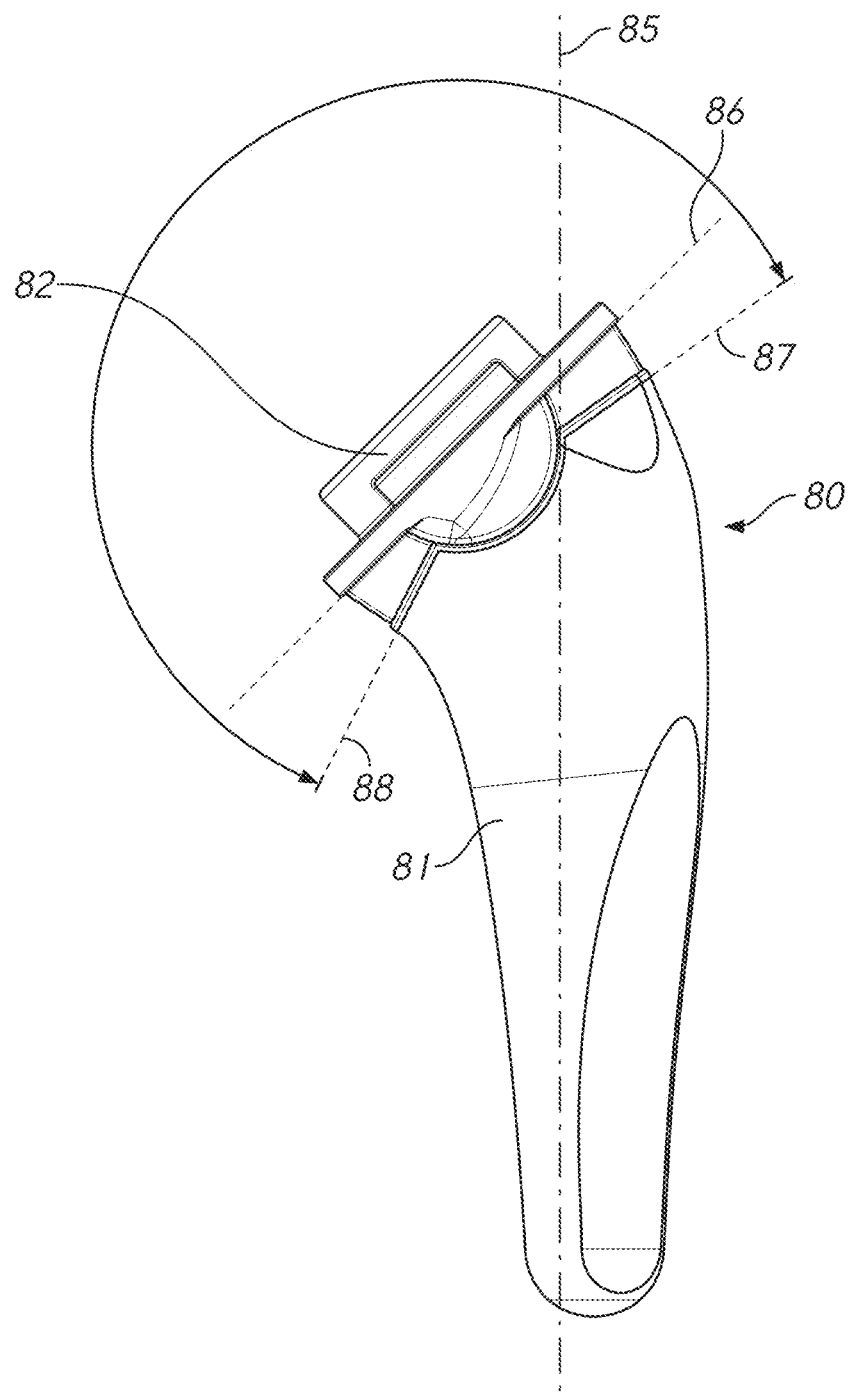
FIG. 84 illustrates a side elevation view of an adjustable angle shoulder prosthesis stem, according to embodiments of the present invention.
Figure 85:
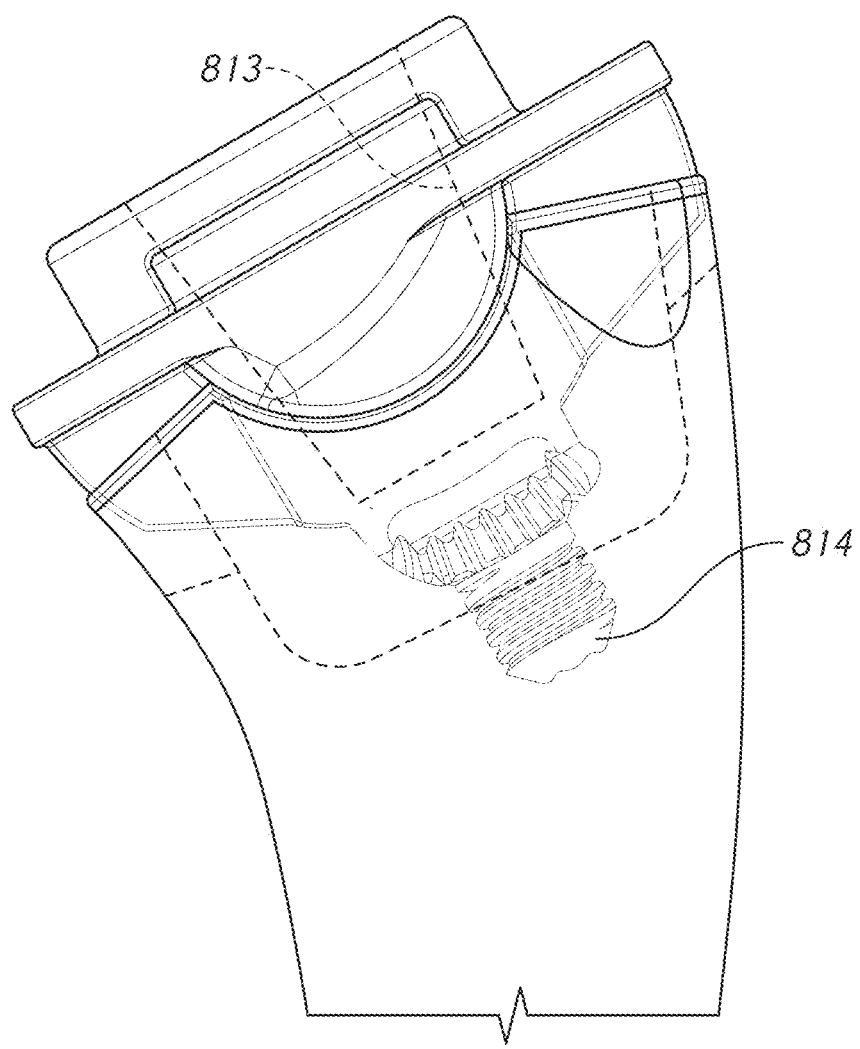
FIG. 85 illustrates a side view of an adjustable angle shoulder prosthesis stem showing an outline of a proximal female stem taper, according to embodiments of the present invention.
Figure 86:
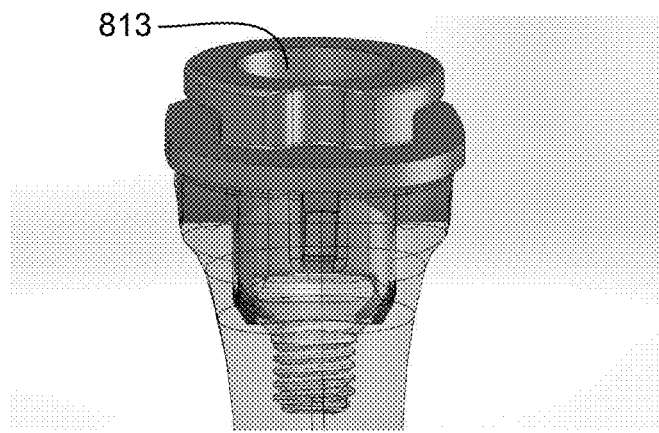
FIG. 86 illustrates a front elevation view of an adjustable angle shoulder prosthesis stem, according to embodiments of the present invention.
Figure 92:
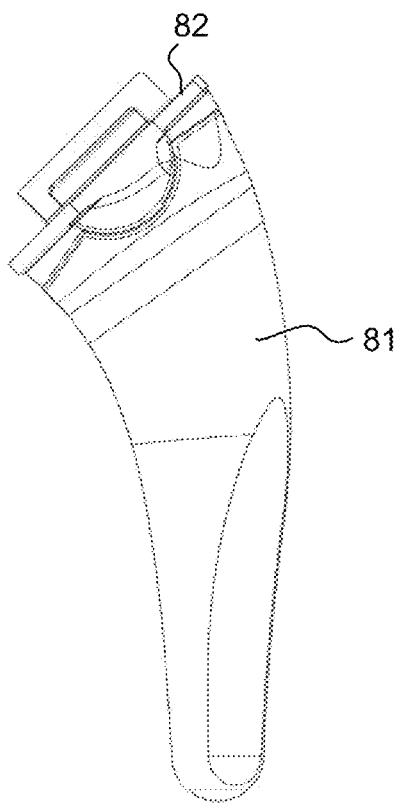
FIG. 92 illustrates a front elevation view of an adjustable angle shoulder prosthesis stem with the proximal stem portion pivoted with respect to the distal stem portion at an intermediate angle about the pivot axis, according to embodiments of the present invention.
Figure 93:
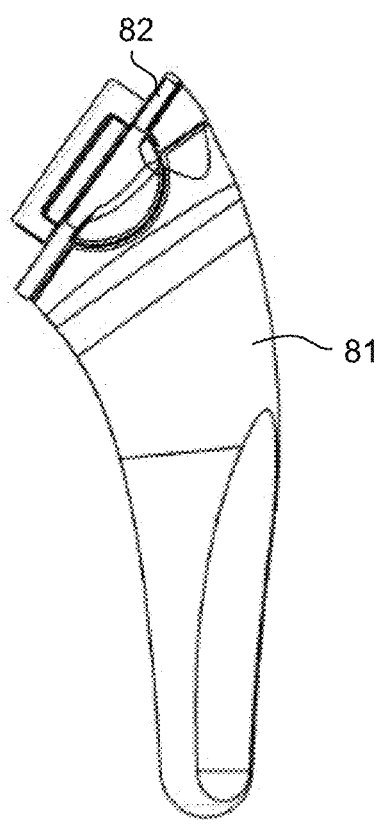
FIG. 93 illustrates a front elevation view of the adjustable angle shoulder prosthesis stem of FIG. 92 with the proximal stem portion pivoted with respect to the distal stem portion to a fully medial angle about the pivot axis, according to embodiments of the present invention.
Figure 94:
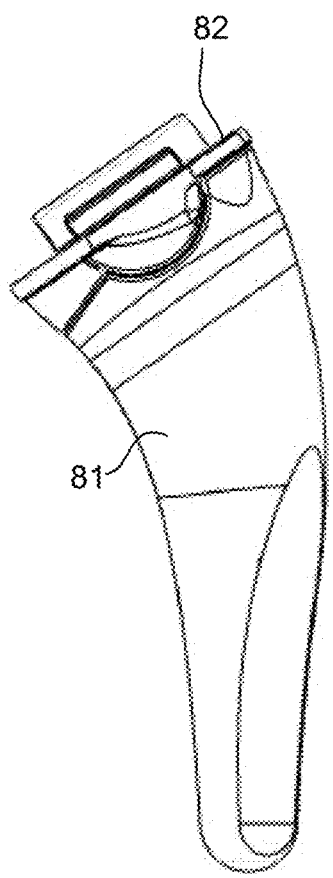
FIG. 94 illustrates a front elevation view of the adjustable angle shoulder prosthesis stem of FIG. 92 with the proximal stem portion pivoted with respect to the distal stem portion to a fully lateral angle about the pivot axis, according to embodiments of the present invention.

FIG. 84 illustrates a range of angles through which the proximal stem portion 82 may be pivoted with respect to the distal stem portion 81, according to embodiments of the present invention. FIG. 84 illustrates a line or plane 86 that is substantially flush with the proximal bearing surface 825; this line 86 is at an angle with respect to the primary stem axis 85, and is shown somewhere within the range of angles. As the proximal stem portion 82 is pivoted laterally, the proximal bearing surface 825 may be pivoted to a point at which it is aligned with line 87; as the proximal portion 82 is pivoted medially, the proximal bearing surface 825 may be pivoted to a point at which it is aligned with line 88. According to some embodiments of the present invention, lines 87 and 88 illustrate the extents of the range of angles; for example, the range of angles may be from 125° to 145°, according to embodiments of the present invention. FIG. 92 illustrates the proximal stem portion 82 rotated about pivot point 92 to an intermediate position with respect to the distal stem portion 81; FIG. 93 illustrates the proximal stem portion 82 rotated fully medially about pivot point 92, for example to an angle of 145°; and FIG. 94 illustrates the proximal stem portion 82 rotated fully laterally about pivot point 92, for example to an angle of 125°. Based on the disclosure provided herein, one of ordinary skill in the art will appreciate that other medial and/or lateral maximum angles may be employed.

According to some embodiments of the present invention, the stem 80 includes stops which limit the lateral and/or medial rotation of the proximal stem portion 82 with respect to the distal stem portion 81, according to embodiments of the present invention. For example, a medial stop may occur when the distal surface 826 contacts the proximal surface 814 (as shown for example in FIG. 93), and a lateral stop may occur when the distal surface 827 contacts the proximal surface 815 (as shown for example in FIG. 94), according to embodiments of the present invention. As such, surfaces 814 and 826 may be referred to as a medial stop, and surfaces 815 and 827 may be referred to as a lateral stop, according to embodiments of the present invention. Other stop mechanisms may be employed; for example, the inner distal surface 828 of fin 822 may be configured to abut the inner proximal surface 816 of the distal stem portion 81 to form a variation of a medial stop, according to embodiments of the present invention. A similar stop mechanism may be created for an alternative lateral stop.

The fins 821, 822 and grooves 811, 812 provide additional lateral stability during rotation of the proximal stem portion 82, according to embodiments of the present invention. In addition, the fins 821, 822 help to create a more aesthetically pleasing radiographic profile, by creating a continuous-looking and/or smooth implant profile despite the pivotable adjustable joint (as illustrated for example in FIG. 87).

Figure 87:
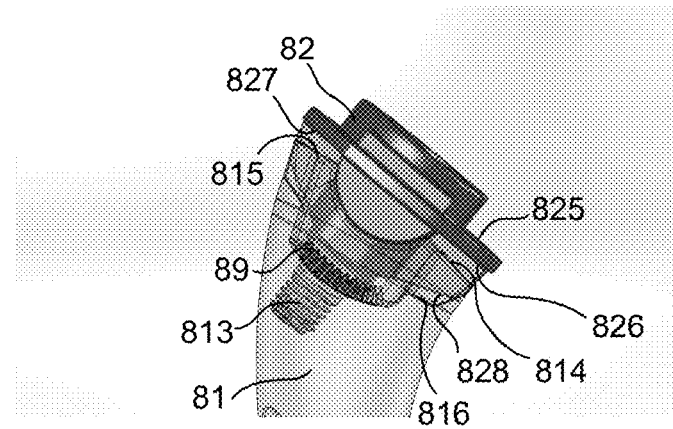
FIG. 87 illustrates a side elevation view of the adjustable angle shoulder prosthesis stem of FIG. 86, according to embodiments of the present invention.

An anti-pivot feature 89 may be included by the proximal stem portion 82 and/or by the distal stem portion 81; for example, as illustrated in FIG. 87, the anti-pivot feature 89 includes teeth and/or grooves 891 formed on the distal end 823 of the proximal stem portion 82 and/or teeth and/or grooves 892 formed on the inner proximal surface 817 of the distal stem portion 82. These teeth and/or grooves 891, 892 permit the rotation about the pivot axis 92 when the distal end 823 is not in contact with the inner proximal surface 817 and/or when no significant force is applied to hold the surfaces in contact with each other. However, once a desired angular placement is achieved, a screw 84 is placed through the female taper 813, with the shaft 841 being inserted through the slot 824 and into engagement with hole 814 to secure the proximal stem portion 82 to the distal stem portion 81, according to embodiments of the present invention. The shaft 841 may be threaded, and the hole 814 may be threaded or tapped to threadably engage with the shaft 841, according to embodiments of the present invention. Once the screw 84 is engaged with hole 814, the proximal stem portion 81 is essentially locked (e.g. does not rotate) with respect to the distal stem portion 82, both due to the pressure of the screw 84 against the top of the slot 824 and due to the friction or interlocking engagement of the anti-pivot feature 89, according to embodiments of the present invention. Other anti-pivot features may be used to further enhance the locking effect of the screw 84, for example rough surface texture, sticky surface texture, bumps, grooves, and other features.

According to some embodiments of the present invention, the pivot axis 92 intersects the proximal stem portion 82, as shown in FIG. 88. This results in a more anatomically correct angle than devices with a pivot axis which is far separated from the resection surface according to embodiments of the present invention. According to some embodiments of the present invention, the stem 80 is implanted such that the resection surface is flush with the proximal bearing surface 825.

Because the adjustable angle prosthesis stem 80 permits a greater range of angles, the same stem 80 may be used for a primary anatomical prosthesis, and then converted to a reverse prosthesis by changing the angle between the proximal and distal stem portions. For example, a prosthetic humeral head (for example, like humeral head H) may be removed from the proximal stem portion 82, and then the proximal stem portion 82 may be unlocked from the distal stem portion 81 by removing or loosening the screw 84 from hole 814. This may be done while the stem 80 is still implanted in the bone, without removing stem 80 from the bone. Then, the proximal stem portion 82 may be pivoted to a different angle, for example from an angle corresponding to a primary anatomical configuration to an angle corresponding to a reverse configuration, and the proximal stem portion 82 may be re-locked to the distal stem portion 81 at the desired angle, for example by reattaching screw 84 through slot 824 and into hole 814. The wide range of angles permitted by the stem 80 also permits the use of a non-angled reverse insert. Existing systems typically require the use of an angled insert to achieve the correct angle for a reverse prosthesis setup, according to embodiments of the present invention.

The stem implant 80 includes an adjustable neck angle as described above. This adjustment is achieved with moving parts that are contained within the shell of the distal stem portion 81. This permits in-vivo adjustments to the inclination. The angular increments by which the proximal stem portion 82 may be adjusted with respect to the distal stem portion 81 are numerous, and may even be described in some cases as nearly infinite or unlimited, according to embodiments of the present invention. The axis 92 about which the proximal stem portion 82 pivots is anatomical, e.g. about the midpoint of the taper base 825, and is also consistent with other stem 10 options described above.

The proximal stem portion 82 incorporates a female taper 813, allowing for revision from a male-tapered head to a reverse adapter, according to embodiments of the present invention. Female taper 813 may be threaded to accept a male-tapered head and/or a reverse adapter, according to embodiments of the present invention. When converting to a reverse, the stem angle may be changed in-situ and/or in-vivo to achieve the desired reverse angle, rather than needing to compensate with angled polymer inserts (which may increase stresses at the insert-adapter interface). Because the angle of stem 80 is adjustable in-situ, trialing may be performed using the final implant (e.g. with the trial head), which may eliminate the need for a trial stem. This has the potential to eliminate many instruments as compared to a typical shoulder prosthesis surgical kit, for example reducing the total number of instruments by two-thirds in some cases. The adjustable angle stem 80 also includes both a female proximal stem taper 813 while also including a female receptacle for receiving the protrusion 823 and/or the proximal stem portion 82, according to embodiments of the present invention. This configuration further aids the implant 80 in keeping an anatomically correct pivot axis 92, according to embodiments of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A reverse shoulder prosthesis, comprising:
   a stem comprising a primary stem axis and an opening in a proximal end of the stem, the proximal opening extending about a metaphyseal axis, the metaphyseal axis at an angle with respect to the primary stem axis;
   a metaphysis comprising:
      a distal end configured for attachment to the stem, the metaphysis being configured to rotate around the metaphyseal axis when coupled to the stem, the metaphysis configured for attachment to the stem at a plurality of rotational positions of the metaphysis about the metaphyseal axis; and
      a proximal end comprising a first interlocking portion having an insert axis that is eccentrically offset from the metaphyseal axis, the first interlocking portion comprising an aperture defining a radially inward facing surface; and
   a reverse insert comprising a proximal end and a distal end, wherein the proximal end of the reverse insert comprises a concave cup formed about a cup axis, and wherein the distal end of the reverse insert comprises a second interlocking portion, the second interlocking portion comprising a protrusion having a radially outward facing surface, the radially outward facing surface being continuous around a periphery of the distal end of the reverse insert,
   wherein an interface between the first and second interlocking portions has a rotational symmetry about the insert axis, and
   wherein the interface between the radially inward facing surface of the first interlocking portion and the radially outward facing surface of the second interlocking portion prevents rotation of the reverse insert relative to the metaphysis about all axes when the reverse insert is engaged with the metaphysis.

2. The prosthesis of claim 1, wherein the metaphysis is configured for attachment to the stem at any rotational position of the metaphysis about the metaphyseal axis.

3. The prosthesis of claim 1, wherein the radially outward facing surface of the second interlocking portion has a cross-sectional shape that is rotationally symmetrical about the insert axis when engaged to the radially inward facing surface of the aperture.

4. The prosthesis of claim 3, wherein the second interlocking portion further comprises a locking lip, and wherein the first interlocking portion further comprises a groove to engage with the locking lip.

5. The prosthesis of claim 4, wherein the locking lip extends around the protrusion, and wherein the groove extends around the aperture.

6. The prosthesis of claim 1, wherein the cup axis is aligned with the insert axis.

7. The prosthesis of claim 1, wherein the cup axis is offset from the insert axis.

8. The prosthesis of claim 1, wherein the reverse insert is an angled insert for which the cup axis is at an angle with respect to the insert axis, such that the reverse insert is configured to lock with the metaphysis in at least two different positions, wherein the cup axis has a different radial orientation with respect to the metaphyseal axis at each of the at least two different positions.

9. The prosthesis of claim 1, wherein the rotational symmetry has an order of six, seven, eight, nine, or ten.

10. The prosthesis of claim 1, wherein the rotational symmetry has an order of eight, a shape of the interface being octagonal.

11. The prosthesis of claim 1, wherein an interface between the metaphysis and the stem comprises a distal-facing surface of the metaphysis and a proximal-facing surface of the stem.

12. The prosthesis of claim 1, wherein the metaphysis is configured such that no part of an interface between the metaphysis and the stem extends outside of a bone when the prosthesis is implanted.

13. A kit for a reverse shoulder prosthesis, the kit comprising:
the reverse shoulder prosthesis of claim 1;
a second stem comprising a second primary stem axis and a second opening in a proximal end of the second stem, the second opening extending about a second metaphyseal axis, the second metaphyseal axis at a second angle with respect to the second primary stem axis, wherein the second angle is different from the angle;
a second reverse insert having a proximal end and a distal end, wherein the proximal end of the second reverse insert comprises a second concave cup formed about a second cup axis, and wherein the distal end of the second reverse insert comprises a third interlocking portion,
wherein an interface surface between the first and third interlocking portions has a rotational symmetry about the insert axis.

14. The kit of claim 13, wherein the reverse insert is a first angled insert for which the corresponding cup axis is at a third, non-zero angle with respect to the insert axis, wherein the second reverse insert is a second angled insert for which the corresponding cup axis is at a fourth, non-zero angle with respect to the insert axis, wherein the fourth angle is different from the third angle.

15. The kit of claim 14, wherein the reverse insert used with the metaphysis and the stem results in a same overall inclination angle as the second reverse insert used with the metaphysis and the second stem.

16. The prosthesis of claim 1, wherein the first interlocking portion comprising a plurality of teeth.

17. The prosthesis of claim 16, wherein the metaphysis is configured for attachment to the stem at any rotational position of the metaphysis about the metaphyseal axis.

18. The prosthesis of claim 16, wherein the cup axis is aligned with the insert axis.

19. The prosthesis of claim 16, wherein the cup axis is offset from the insert axis.

20. A kit for a reverse shoulder prosthesis, the kit comprising:
the reverse shoulder prosthesis of claim 16;
a second stem comprising a second proximal opening and a second primary stem axis, the second opening extending about a second metaphyseal axis, the second metaphyseal axis at a second angle with respect to the second primary stem axis, wherein the second angle is different from the angle;
a second reverse insert having a proximal end and a distal end, wherein the proximal end of the second reverse insert comprises a second concave cup formed about a second cup axis, and wherein the distal end of the second reverse insert comprises a third interlocking portion,
wherein an interface surface between the first and third interlocking portions has a rotational symmetry about the insert axis.

21. The kit of claim 20, wherein the reverse insert is a first angled insert for which the corresponding cup axis is at a third, non-zero angle with respect to the insert axis, wherein the second reverse insert is a second angled insert for which the corresponding cup axis is at a fourth, non-zero angle with respect to the insert axis, wherein the fourth angle is different from the third angle.

22. The kit of claim 21, wherein the reverse insert used with the metaphysis and the distal stem results in a same overall inclination angle as the second reverse insert used with the metaphysis and the second distal stem.

* * * * *